(12) United States Patent
Kishi et al.

(10) Patent No.: US 11,013,668 B2
(45) Date of Patent: May 25, 2021

(54) TWO-PACKAGE DENTAL ADHESIVE COMPOSITION

(71) Applicant: TOKUYAMA DENTAL CORPORATION, Tokyo (JP)

(72) Inventors: Hiroto Kishi, Tokyo (JP); Kazuhiko Okishio, Tokyo (JP); Kyouko Takita, Tokyo (JP)

(73) Assignee: TOKUYAMA DENTAL CORPORATION

( * ) Notice: Subject to any disclaimer, the term of this patent is extended or adjusted under 35 U.S.C. 154(b) by 0 days.

(21) Appl. No.: 16/317,112

(22) PCT Filed: Aug. 9, 2017

(86) PCT No.: PCT/JP2017/028926
§ 371 (c)(1),
(2) Date: Jan. 11, 2019

(87) PCT Pub. No.: WO2018/034212
PCT Pub. Date: Feb. 22, 2018

(65) Prior Publication Data
US 2019/0240117 A1  Aug. 8, 2019

(30) Foreign Application Priority Data

Aug. 18, 2016  (JP) .............................. JP2016-160395
Aug. 18, 2016  (JP) .............................. JP2016-160396

(51) Int. Cl.
| | | |
|---|---|---|
| A61K 6/887 | (2020.01) | |
| A61K 6/30 | (2020.01) | |
| A61K 6/00 | (2020.01) | |
| A61K 6/62 | (2020.01) | |
| A61K 6/896 | (2020.01) | |
| C08F 222/10 | (2006.01) | |
| C08F 228/06 | (2006.01) | |
| C08F 230/02 | (2006.01) | |

(52) U.S. Cl.
CPC .................. *A61K 6/30* (2020.01); *A61K 6/00* (2013.01); *A61K 6/62* (2020.01); *A61K 6/887* (2020.01); *A61K 6/896* (2020.01); *C08F 222/103* (2020.02); *C08F 228/06* (2013.01); *C08F 230/02* (2013.01)

(58) Field of Classification Search
CPC ..................................................... A61K 6/887
See application file for complete search history.

(56) References Cited

U.S. PATENT DOCUMENTS

| | | |
|---|---|---|
| 2002/0132951 A1 | 9/2002 | Ibaragi et al. |
| 2003/0050359 A1 | 3/2003 | Kimura et al. |
| 2009/0076182 A1 | 3/2009 | Tanaka et al. |
| 2010/0240796 A1 | 9/2010 | Bock et al. |
| 2010/0261144 A1 | 10/2010 | Fujinami et al. |
| 2010/0304961 A1 | 12/2010 | Kimura et al. |

FOREIGN PATENT DOCUMENTS

| | | |
|---|---|---|
| CN | 1365269 A | 8/2002 |
| CN | 101868218 A | 10/2010 |
| JP | H7-187941 A | 7/1995 |
| JP | H7-187942 A | 7/1995 |
| JP | 2002-161013 A | 6/2002 |
| JP | 2002-187907 A | 7/2002 |
| JP | 2002-265312 A | 9/2002 |
| JP | 2004-043427 A | 2/2004 |
| JP | 2005-239560 A | 9/2005 |
| JP | 2006-045094 A | 2/2006 |
| JP | 2008-024668 A | 2/2008 |
| JP | 2008-056649 A | 3/2008 |
| JP | 2009-007280 A | 1/2009 |
| JP | 2009-067746 A | 4/2009 |
| JP | 2009-127000 A | 6/2009 |
| JP | 2010-202625 A | 9/2010 |
| JP | 2010-215624 A | 9/2010 |
| JP | 2014-152106 A | 8/2014 |
| JP | 2014-152107 A | 8/2014 |
| JP | 2017218407 A | 12/2017 |

(Continued)

OTHER PUBLICATIONS

English machine translation Kazama et al. (JP 2002-265312) (Year: 2002).*
Extended European Search Report for Application No. 17 841 435.5 dated Feb. 13, 2020 (11 pages).
Australian Office Action for Application No. 2017-311835 dated May 29, 2019 (8 pages).
Barry Arkles, Silane Coupling Agents: Connecting Across Boundaries brochure, 3rd Edition, 2014, Morrisville, PA.
Japanese Office Action for corresponding Application No. 2016-160395 dated Jun. 2, 2020 (8 pages) with English translation.

(Continued)

*Primary Examiner* — Michael F Pepitone
(74) *Attorney, Agent, or Firm* — Harness, Dickey & Pierce, P.L.C.

(57) ABSTRACT

A two-package dental adhesive composition is provided that has an excellent adhesive property for each of various dental materials and also has excellent storage stability. The two-package dental adhesive composition includes a first agent and a second agent which are divided from each other. The two-package dental adhesive composition includes at least five components including: (A) an acidic group-containing polymerizable monomer; (B) a sulfur atom-containing polymerizable monomer; (C) a silane coupling agent; (D) a borate compound; and (E) water. The first agent contains only (A) the acidic group-containing polymerizable monomer and (B) the sulfur atom-containing polymerizable monomer out of the five components. The second agent contains only (C) the silane coupling agent, (D) the borate compound, and (E) the water out of the five components.

16 Claims, No Drawings

(56) References Cited

FOREIGN PATENT DOCUMENTS

NO          3061072  A1    10/2000

OTHER PUBLICATIONS

Japanese Office Action for corresponding Application No. 2016-160396 dated Jun. 2, 2020 (5 pages) with English translation.
Decision to Grant a Patent for JP Application No. 2016-160396, dated Jan. 12, 2021 (3 pages).

\* cited by examiner

TWO-PACKAGE DENTAL ADHESIVE COMPOSITION

This application is a U.S. National Stage Application of International Application No. PCT/JP2017/028926, filed on Aug. 9, 2017, and published in Japanese as WO 2018/034212 A1 on Feb. 22, 2018 and claims priority to Japanese Application Nos. 2016-160395 and 2016-160396, both filed on Aug. 18, 2016. The entire disclosures of the above applications are expressly incorporated herein by reference.

BACKGROUND

Technical Field

The present invention relates to a two-package dental adhesive composition.

Related Art

In dental clinical practice, various restoration materials are used for portions having defects caused by caries, an accident, and the like. For example, a composite resin is used for a small cavity, and a dental crown material made of ceramics, a metal, or the like is used for a large defective portion. In addition, when restoration is performed after pulpectomy, a resin core is used in order to form an abutment tooth as a scaffold.

Various adhesives are used in order to bond those materials to a tooth substance. For example, in general, a photopolymerizable bonding material is used for the composite resin, dental cement and its pretreatment material (primer) are used for the dental crown material, and a dual-cure bonding material, which contains a photopolymerization catalyst and a chemical polymerization catalyst, is used for the resin core. However, when each adhesive is used properly according to each case, a clinical operation becomes complicated.

Therefore, in order to cope with such problem, there has been proposed a dental primer composition that expresses a sufficient adhesive property for each of the tooth substance, the metal, and the ceramics (for example, JP 2002-265312 A). In this connection, in JP 2002-265312, there is a disclosure that a primer composition obtained by mixing a coupling agent, a sulfur atom-containing polymerizable compound, an acidic group-containing polymerizable compound, a polymerizable monomer, an organic solvent, and water, or a primer composition obtained by further adding a polymerization accelerator to the above-mentioned primer composition has provided excellent adhesive strength for each of the tooth substance, the metal, and the ceramics.

Meanwhile, a dental adhesive that expresses an excellent adhesive property for each of various dental materials, such as a tooth substance, a metal, and ceramics, is required to be able to maintain an excellent adhesive property even after long-term storage.

The present invention has been made in view of the above-mentioned circumstances, and an object of the present invention is to provide a two-package dental adhesive composition excellent in adhesive property for each of various dental materials and also excellent in storage stability.

SUMMARY

The above-mentioned object is achieved by embodiments of the present invention to be described below.

That is, according to one embodiment of the present invention, there is provided a two-package dental adhesive composition including a first agent and a second agent, which are divided from each other, the two-package dental adhesive composition including at least five components including: (A) an acidic group-containing polymerizable monomer; (B) a sulfur atom-containing polymerizable monomer; (C) a silane coupling agent; (D) a borate compound; and (E) water, wherein the first agent contains only (A) the acidic group-containing polymerizable monomer and (B) the sulfur atom-containing polymerizable monomer out of the five components, and wherein the second agent contains only (C) the silane coupling agent, (D) the borate compound, and (E) the water out of the five components.

In a two-package dental adhesive composition according to one embodiment of the present invention, it is preferred that a blending ratio of (A) the acidic group-containing polymerizable monomer with respect to 100 parts by mass of all polymerizable monomers including at least (A) the acidic group-containing polymerizable monomer and (B) the sulfur atom-containing polymerizable monomer be from 5 parts by mass to 30 parts by mass.

In a two-package dental adhesive composition according to another embodiment of the present invention, it is preferred that (A) the acidic group-containing polymerizable monomer to be used include an acidic group-containing polymerizable monomer represented by the following general formula (A1) and an acidic group-containing polymerizable monomer represented by the following general formula (A2), and a blending ratio of the acidic group-containing polymerizable monomer represented by the general formula (A2) to a total amount of the acidic group-containing polymerizable monomer represented by the general formula (A1) and the acidic group-containing polymerizable monomer represented by the general formula (A2) be from 3 mass % to 40 mass %:

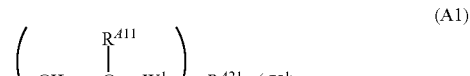

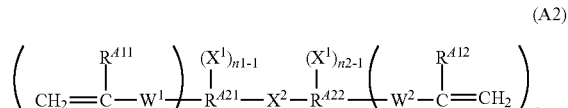

in the general formula (A1), $R^{A11}$ represents a hydrogen atom or a methyl group, $W^1$ represents an oxycarbonyl group (—COO—), an iminocarbonyl group (—CONH—), or a phenylene group (—C$_6$H$_4$—), $R^{A21}$ represents (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, $X^1$ represents a monovalent acidic group, m1 represents an integer of from 1 to 4, n1 represents an integer of from 1 to 6−m1, and m1+n1 represents a valence of $R^{A21}$; and in the general formula (A2), $R^{A11}$ and $R^{A12}$ each independently represent a hydrogen atom or a methyl group, $W^1$ and $W^2$ each independently represent an oxycarbonyl group (—COO—), an iminocarbonyl group (—CONH—), or a phenylene group (—C$_6$H$_4$—), $R^{A21}$ and $R^{A22}$ each independently represent (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, $X^1$ represents a monovalent acidic group, $X^2$ represents a divalent acidic group, m1 and m2 each independently represent an integer of from 1 to 4, n1 represents an integer of from 1 to 6−m1, n2 represents an integer of from 1 to 6−m2, m1+n1 represents a valence of $R^{A21}$, and m2+n2 represents a valence of $R^{A22}$.

In a two-package dental adhesive composition according to another embodiment of the present invention, it is preferred that (A) the acidic group-containing polymerizable monomer to be used include a long-chain phosphoric acid group-containing polymerizable monomer represented by the following general formula (A1) and a short-chain phosphoric acid group-containing polymerizable monomer represented by the following general formula (A2):

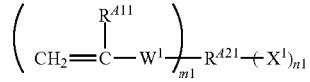
(A1)

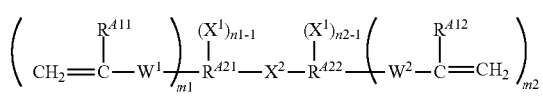
(A2)

in the general formula (A1), $R^{A11}$ represents a hydrogen atom or a methyl group, $W^1$ represents an oxycarbonyl group (—COO—), an iminocarbonyl group (—CONH—), or a phenylene group (—$C_6H_4$—), $R^{A21}$ represents a 2- to 6-valent chain hydrocarbon group having 6 to 14 carbon atoms in a main chain thereof, or a 2- to 6-valent chain organic residue containing at least one bond selected from an ether bond and an ester bond in a main chain thereof and having 6 to 14 atoms in the main chain, $X^1$ represents a dihydrogen phosphate monoester group {—O—P(=O)(OH)$_2$} or a phosphono group {—P(=O)(OH)$_2$}, m1 represents an integer of from 1 to 4, n1 represents an integer of from 1 to 6−m1, and m1+n1 represents a valence of $R^{A21}$; and in the general formula (A2), $R^{A11}$ and $R^{A12}$ each independently represent a hydrogen atom or a methyl group, $W^1$ and $W^2$ each independently represent an oxycarbonyl group (—COO—), an iminocarbonyl group (—CONH—), or a phenylene group (—$C_6H_4$—), $R^{A21}$ and $R^{A22}$ each independently represent a 2- to 6-valent chain hydrocarbon group having 2 to 4 carbon atoms in a main chain thereof, or a 2- to 6-valent chain organic residue containing at least one bond selected from an ether bond and an ester bond in a main chain thereof and having 2 to 4 atoms in the main chain, $X^1$ represents a monovalent acidic group, $X^2$ represents a hydrogen phosphate diester group {(—O—)$_2$P(=O)OH} or a phosphinico group {=P(=O)OH}, m1 and m2 each independently represent an integer of from 1 to 4, m1+n1 represents a valence of $R^{A21}$, m2+n2 represents a valence of $R^{A22}$, n1 represents an integer of from 1 to 6−m1, and n2 represents an integer of from 1 to 6−m2.

In a two-package dental adhesive composition according to another embodiment of the present invention, it is preferred that (C) the silane coupling agent include a compound represented by the following general formula (C$_1$):

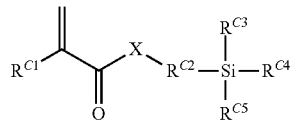
(C1)

in the general formula (C1), X represents an oxygen atom or a nitrogen atom, $R^{C1}$ represents a methyl group or a hydrogen atom, $R^{C2}$ represents an alkylene group having 1 to 10 carbon atoms, and $R^{C3}$, $R^{C4}$, and $R^{C5}$ each independently represent an alkyl group having 1 to 10 carbon atoms or an alkoxyl group having 1 to 10 carbon atoms, provided that at least one group selected from $R^{C3}$, $R^{C4}$, and $R^{C5}$ is an alkoxy group having 2 to 4 carbon atoms.

In a two-package dental adhesive composition according to another embodiment of the present invention, it is preferred that, in the general formula (C1), $R^{C3}$, $R^{C4}$, and $R^{C5}$ each independently represent an alkoxyl group having 2 to 4 carbon atoms.

In a two-package dental adhesive composition according to another embodiment of the present invention, it is preferred that (D) the borate compound include an alkali metal salt of a tetraarylborate.

In a two-package dental adhesive composition according to another embodiment of the present invention, it is preferred that at least one of the first agent or the second agent further contain (F) an organic solvent, (F) the organic solvent include at least a low-boiling-point organic solvent having a boiling point of from 50° C. to 65° C. at normal pressure, and a high-boiling-point organic solvent having a boiling point of from 75° C. to 90° C. at normal pressure, a blending ratio of the low-boiling-point organic solvent with respect to 100 parts by mass of polymerization-reactive components including at least (A) the acidic group-containing polymerizable monomer, (B) the sulfur atom-containing polymerizable monomer, and (C) the silane coupling agent be from 200 parts by mass to 400 parts by mass, and a blending ratio of the high-boiling-point organic solvent with respect to 100 parts by mass of the polymerization-reactive components be from 25 parts by mass to 120 parts by mass.

In a two-package dental adhesive composition according to another embodiment of the present invention, it is preferred that a blending ratio of (E) the water with respect to 100 parts by mass of the polymerization-reactive components be from 5 parts by mass to 50 parts by mass.

In a two-package dental adhesive composition according to another embodiment of the present invention, it is preferred that a mass ratio of the low-boiling-point organic solvent to the high-boiling-point organic solvent be from 2 to 12.

In a two-package dental adhesive composition according to another embodiment of the present invention, it is preferred that the two-package dental adhesive composition further include an organic peroxide and a vanadium compound.

In a two-package dental adhesive composition according to another embodiment of the present invention, it is preferred that in each of (i) a case in which the two-package dental adhesive composition contains only (D) the borate compound blended into the second agent as a chemical polymerization initiator, and (ii) a case in which the two-package dental adhesive composition contains each of (D) the borate compound blended into the second agent, and a chemical polymerization initiator other than (D) the borate compound, which is blended into at least one of the first agent or the second agent, as the chemical polymerization initiator, when a mixture obtained by mixing, at 23° C., only a whole amount of the polymerization-reactive components and a whole amount of the chemical polymerization initiator containing at least (D) the borate compound is prepared, a curing time commencing immediately after the mixing and ending on completion of curing of the mixture be 60 seconds or less.

In a two-package dental adhesive composition according to another embodiment of the present invention, it is preferred that the first agent further contain (F) an organic solvent, and a blending ratio of (F) the organic solvent in the first agent be from 30 mass % to 90 mass %.

In a two-package dental adhesive composition according to another embodiment of the present invention, it is preferred that the second agent further contain (F) an organic solvent, and a blending ratio of (F) the organic solvent in the second agent be from 10 mass % to 99 mass %.

In a two-package dental adhesive composition according to another embodiment of the present invention, it is preferred that the first agent and the second agent each further contain (F) an organic solvent, and a ratio of a total amount of (F) the organic solvent to a total amount of the first agent and the second agent be from 63 mass % to 85 mass %.

Advantageous Effects of Invention

As described above, according to the present invention, the two-package dental adhesive composition excellent in adhesive property for each of various dental materials and also excellent in storage stability can be provided.

DETAILED DESCRIPTION

Two-package Dental Adhesive Composition

A two-package dental adhesive composition according to an embodiment of the present invention includes a first agent and a second agent, which are divided from each other, and includes at least five components including (A) an acidic group-containing polymerizable monomer, (B) a sulfur atom-containing polymerizable monomer, (C) a silane coupling agent, (D) a borate compound, and (E) water. In addition, the first agent contains only (A) the acidic group-containing polymerizable monomer and (B) the sulfur atom-containing polymerizable monomer out of the five components set forth in the (A) to (E), and the second agent contains only (C) the silane coupling agent, (D) the borate compound, and (E) the water out of the five components set forth in the (A) to (E).

The first agent does not contain the components set forth in (C) to (E) out of the five components set forth in the (A) to (E) in principle, but is permitted to inevitably contain trace amounts of the components set forth in (C) to (E) in the form of impurities or the like. Likewise, the second agent does not contain the components set forth in (A) and (B) out of the five components set forth in the (A) to (E) in principle, but is permitted to inevitably contain trace amounts of the components set forth in (A) and (B) in the form of impurities or the like.

Here, (A) the acidic group-containing polymerizable monomer mainly improves an adhesive property for each of a tooth substance (dentin or enamel), a base metal (iron, nickel, chromium, cobalt, tin, aluminum, copper, titanium, or the like, or an alloy containing any such metal as a main component), and a metal oxide containing a metal, such as zirconium, and oxygen as main components (zirconia ceramics, alumina, titania, or the like), (B) the sulfur atom-containing polymerizable monomer mainly improves an adhesive property for a noble metal (gold, platinum, palladium, silver, or the like, or an alloy containing any such metal as a main component), and (C) the silane coupling agent mainly improves an adhesive property for each of a silica-based oxide containing silicon oxide as a component (porcelain, silica particles, silica-based glass ceramics, silica-based glass, or the like) and a composite resin material (material obtained by compositing a resin matrix and an inorganic filler containing a silica-based oxide, such as silica particles or silica-based glass fiber, as a component).

Accordingly, the two-package dental adhesive composition according to this embodiment can exhibit an excellent adhesive property for each of various dental materials, such as a tooth substance, metals (base metal and noble metal), a metal oxide, a silica-based oxide, and a composite resin material.

In addition, (D) the borate compound functions as a polymerization accelerator for accelerating the polymerization and curing of a mixed composition obtained by mixing the first agent and the second agent with each other, and hence has a function of further improving the adhesive property for each of various adherends. In addition, when a chemically polymerizable dental composition (e.g., resin cement) containing an organic peroxide and an amine compound is bonded to a dental material, such as a tooth substance, metals (base metal and noble metal), a metal oxide, a silica-based oxide, or a composite resin material, through the use of the two-package dental adhesive composition according to this embodiment, (D) the borate compound can also suppress a significant reduction in adhesive strength by suppressing a reduction in polymerization activity of the chemically polymerizable dental composition due to (A) the acidic group-containing polymerizable monomer.

Further, (E) the water has functions of: improving an adhesive property for a tooth substance by decalcifying the surface of the tooth substance in the presence of (A) the acidic group-containing polymerizable monomer, which is a kind of acid component; and improving an adhesive property for each of a silica-based oxide and a composite resin material in the presence of (C) the silane coupling agent. In addition, the two-package dental adhesive composition according to this embodiment exhibits an adhesive property when the first agent and the second agent are mixed with each other and applied to the surface of an adherend to allow the progress of chemical polymerization and the like through an interaction between each of the above-mentioned components and the adherend, and an interaction between the above-mentioned components.

Meanwhile, a mixed composition obtained by mixing the five components set forth in the (A) to (E) at one time can exhibit an excellent adhesive property for each of a tooth substance, a base metal, a noble metal, a metal oxide, a silica-based oxide, and a composite resin material immediately after the mixing, but eventually becomes unable to be used as an adhesive through the progress of gelation when stored for a long period of time. The progress of the gelation of the mixed composition is presumably due to an interaction between any two or more components out of the five components set forth in (A) to (E), but the details thereof are unknown. However, as a result of trial and error, the inventors of the present invention have found that, when the five components set forth in (A) to (E) are stored in the form of being separated into the first agent containing (A) the acidic group-containing polymerizable monomer and (B) the sulfur atom-containing polymerizable monomer, and the second agent containing (C) the silane coupling agent, (D) the borate compound, and (E) the water, an excellent adhesive property can be secured for each of various dental materials, and besides, excellent storage stability can also be obtained.

The first agent may further contain a component other than (A) the acidic group-containing polymerizable monomer and (B) the sulfur atom-containing polymerizable monomer (provided that components falling under the categories of the (C) to (E) are excluded) as required, and the second agent may further contain a component other than (C) the silane coupling agent, (D) the borate compound, and (E) the water (provided that components falling under the categories of the (A) and (B) are excluded) as required. The details of the other components that may be further added to the first agent and the second agent are described later. In addition, it is particularly preferred that the second agent does not contain any acid component other than (A) the acidic group-containing polymerizable monomer, either. This is because, when the second agent contains an acid component, the acid component accelerates the hydrolysis of a hydrolyzable group, such as an alkoxy group, contained in (C) the silane coupling agent, or causes a decomposition reaction of (D) the borate compound, with the result that the storage stability of the second agent is liable to be significantly reduced during storage.

Herein, that "the second agent does not contain any acid component" means that the second agent contains substantially no acid component, and it is particularly preferred that the second agent contain no acid component at all. In other words, a case in which the second agent contains a trace amount of an acid component as an impurity or the like is permitted as long as adhesive strength after long-term storage and storage stability are not adversely affected. In addition, the term "acid component" means a substance having a pH of 4 or less as an aqueous solution or an aqueous dispersion when dissolved and/or dispersed in water at a concentration of 1 mol/L. Examples of the "acid component" include any known acid components including inorganic acids, such as hydrochloric acid and nitric acid, and organic acids, such as acetic acid and citric acid, in particular, acid components to be used for dental compositions, such as: a polymerizable monomer containing an acidic group, such as a phosphoric acid group, a phosphonic acid group, a sulfonic acid group, or a carboxyl group; and a filler having a surface modified with an acidic group, such as a phosphoric acid group, a phosphonic acid group, a sulfonic acid group, or a carboxyl group.

In addition, when stored, the two-package dental adhesive composition according to this embodiment is stored in a state of being divided into the first agent and the second agent. Herein, the form of the dividing is not particularly limited as long as a composition constituting the first agent and a composition constituting the second agent are not brought into contact and mixed with each other during storage. In ordinary cases, the first agent and the second agent are each separately stored in any of various containers, such as a syringe, a bag, and a bottle. Meanwhile, at the time of use, in ordinary cases, the first agent and the second agent are mixed with each other to prepare a mixed composition, and then the mixed composition is applied to the surface of an adherend, such as a tooth substance. However, it is also possible to mix the first agent and the second agent with each other on the surface of the adherend by simultaneously applying or separately and sequentially applying the first agent and the second agent to the surface of the adherend.

A mixing ratio (first agent/second agent) between the first agent and the second agent at the time of the use of the two-package dental adhesive composition according to this embodiment may be appropriately selected within a range in which the adhesive property and workability are not significantly impaired. From the viewpoints of practical use, such as handleability and ease of product packaging, the mixing ratio (first agent/second agent) falls within the range of preferably from 1/5 to 5/1, more preferably from 1/3 to 3/1 in terms of volume ratio, or falls within the range of preferably from 1/5 to 5/1, more preferably from 1/3 to 3/1 in terms of mass ratio. In addition, a user of the two-package dental adhesive composition according to this embodiment generally mixes the first agent and the second agent with each other in accordance with a mixing ratio specified by a developer, manufacturer, or seller of the two-package dental adhesive composition according to this embodiment (hereinafter referred to as "specified mixing ratio"). An actual mixing ratio at the time of use is permitted to deviate from the specified mixing ratio within a range in which the adhesive property and the workability are not significantly impaired, and for example, the actual mixing ratio at the time of use in the case where the specified mixing ratio serves as a reference (100%) may fall within the range of from 33% to 300%, and preferably falls within the range of from 50% to 200%.

The specified mixing ratio may be indicated on a mixing ratio information indication medium. As the mixing ratio information indication medium, for example, there may be utilized: i) a product package formed of a paper box or the like; ii) an instruction manual for a product to be supplied as a paper medium and/or electronic data; iii) a container (e.g., a bottle, a syringe, or a packaging bag) for storing each of the first agent and the second agent in a sealed state; iv) a product catalog to be supplied as a paper medium and/or electronic data; or v) a written message to be sent to a product user by email, mail matter, or the like separately from a product. In addition, the specified mixing ratio may be provided to a product user in a mode allowing the specified mixing ratio to be recognized by the product user other than the modes set forth in the i) to v).

With regard to a component X and a component Y to be used for the two-package dental adhesive composition according to this embodiment, when parts of the component X and the component Y are contained in the first agent and the remaining parts are contained in the second agent, a blending ratio Z of the component Y with respect to the blending amount of the component X disclosed herein serving as a reference amount means that the first agent and the second agent are mixed with each other as described below. That is, it is meant that the first agent and the second agent are mixed with each other at such a mixing ratio as to satisfy the blending ratio Z.

Next, the details of each component to be used for the two-package dental adhesive composition according to this embodiment are described.

(A) Acidic Group-Containing Polymerizable Monomer

The acidic group-containing polymerizable monomer to be blended into the first agent means a compound having, in the molecule, one or more acidic groups and one or more polymerizable unsaturated groups. Here, examples of the acidic group include groups each showing acidity in an aqueous solution, such as a phosphinico group $\{=P(=O)OH\}$, a phosphono group $\{-P(=O)(OH)_2\}$, a carboxyl group $\{-C(=O)OH\}$, a dihydrogen phosphate monoester group $\{-O-P(=O)(OH)_2\}$, a hydrogen phosphate diester group $\{(-O-)_2P(=O)OH\}$, a sulfo group $(-SO_3H)$, and organic groups each having an acid anhydride skeleton $\{-C(=O)-O-C(=O)-\}$. In addition, examples of the polymerizable unsaturated group include an acryloyl group, a methacryloyl group, an acrylamide group, a methacrylamide group, and a styryl group.

The acidic group-containing polymerizable monomer is not particularly limited as long as the acidic group-containing polymerizable monomer is a compound having, in the molecule, one or more acidic groups and one or more polymerizable unsaturated groups. From the viewpoint of adhesive strength for a tooth substance or a base metal, a compound represented by the following general formula (A1) or (A2) may be suitably used.

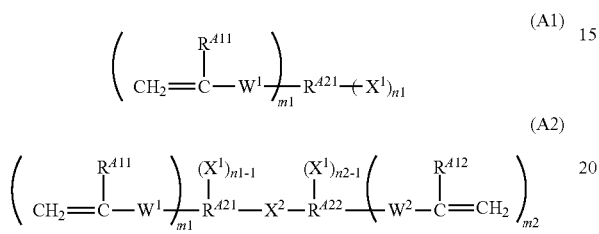

In the general formula (A1), $R^{A11}$ represents a hydrogen atom or a methyl group, $W^1$ represents an oxycarbonyl group (—COO—), an iminocarbonyl group (—CONH—), or a phenylene group (—C$_6$H$_4$—), $R^{A21}$ represents (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, and $X^1$ represents a monovalent acidic group.

In addition, m1 represents an integer of from 1 to 4, n1 represents an integer of from 1 to 6–m1, and m1+n1 represents a valence of $R^{A21}$.

When $W^1$ represents an oxycarbonyl group or an iminocarbonyl group, anyone of (ii) the hydrocarbon group or (iii) the organic residue is selected as $R^{A21}$. In addition, when a bonding site is selected as $R^{A21}$, m1=n1=1.

In the general formula (A2), $R^{A11}$ and $R^{A12}$ each independently represent a hydrogen atom or a methyl group, $W^1$ and $W^2$ each independently represent an oxycarbonyl group (—COO—), an iminocarbonyl group (—CONH—), or a phenylene group (—C$_6$H$_4$—), $R^{A21}$ and $R^{A22}$ each independently represent (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, $X^1$ represents a monovalent acidic group, and $X^2$ represents a divalent acidic group.

In addition, m1 and m2 each independently represent an integer of from 1 to 4, n1 represents an integer of from 1 to 6–m1, n2 represents an integer of from 1 to 6–m2, m1+n1 represents a valence of $R^{A21}$, and m2+n2 represents a valence of $R^{A22}$.

When $W^1$ represents an oxycarbonyl group or an iminocarbonyl group, anyone of (ii) the hydrocarbon group or (iii) the organic residue is selected as $R^{A21}$, and when $W^2$ represents an oxycarbonyl group or an iminocarbonyl group, any one of (ii) the hydrocarbon group or (iii) the organic residue is selected as $R^{A22}$.

In addition, when $R^{A21}$ represents a bonding site, m1=n1=1, and when $R^{A22}$ represents a bonding site, m2=n2=1.

In the general formulae (A1) and (A2), as long as $X^1$ and $X^2$ each represent an acidic group conforming to the above-mentioned definition, their structures are not particularly limited, but preferred specific examples are as shown below.

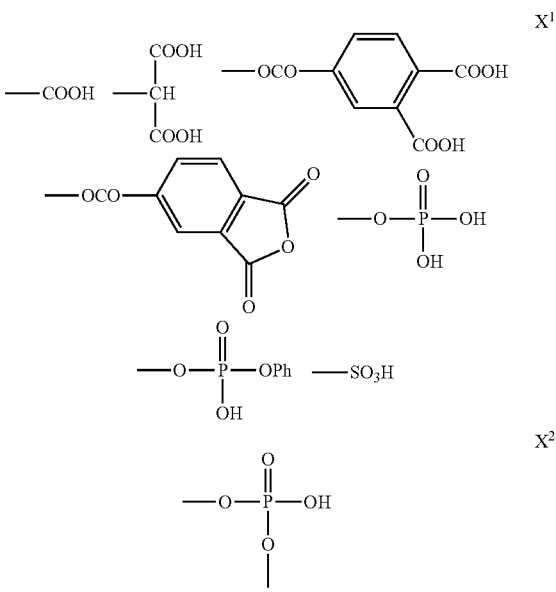

In the general formulae (A1) and (A2), the structures of $R^{A21}$ and $R^{A22}$ are not particularly limited, and (i) the bonding site, (ii) the hydrocarbon group, or (iii) the organic residue may be adopted, but specific examples of suitable groups are as shown below. In the specific examples of $R^{A21}$ and $R^{A22}$ shown below, p1, p2, and p3 each independently represent an integer of from 0 to 10, and p1+p2+p3 is 1 or more.

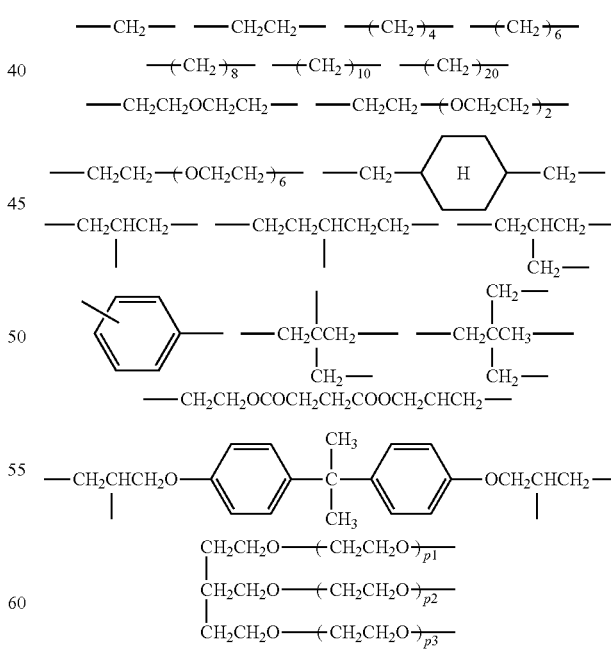

In the general formula (A1), a case in which $R^{A21}$ represents a bonding site refers to a state in which m1=n1=1 and the group $W^1$ and the group $X^1$ are directly bonded to each other. In addition, when $W^1$ represents an oxycarbonyl group or an iminocarbonyl group, anyone of (ii) the hydrocarbon group or (iii) the organic residue is selected as $R^{A21}$.

In addition, in the general formula (A2), a case in which $R^{A21}$ represents a bonding site refers to a state in which m1=n1=1 and the group $W^1$ and the group $X^2$ are directly bonded to each other. In addition, when $W^1$ represents an oxycarbonyl group or an iminocarbonyl group, any one of (ii) the hydrocarbon group or (iii) the organic residue is selected as $R^{A21}$. Similarly, a case in which $R^{A22}$ represents a bonding site refers to a state in which m2=n2=1 and the group $W^2$ and the group $X^2$ are directly bonded to each other. In addition, when $W^2$ represents an oxycarbonyl group or an iminocarbonyl group, any one of (ii) the hydrocarbon group or (iii) the organic residue is selected as $R^{A22}$.

Preferred specific examples of the acidic group-containing polymerizable monomers represented by the general formulae (A1) and (A2) are shown below. In the specific examples shown below, Ph represents a phenyl group, and $R^{411}$ is the same as that shown in the general formula (A1) or (A2).

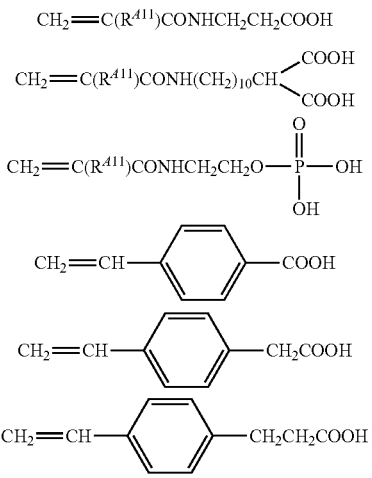

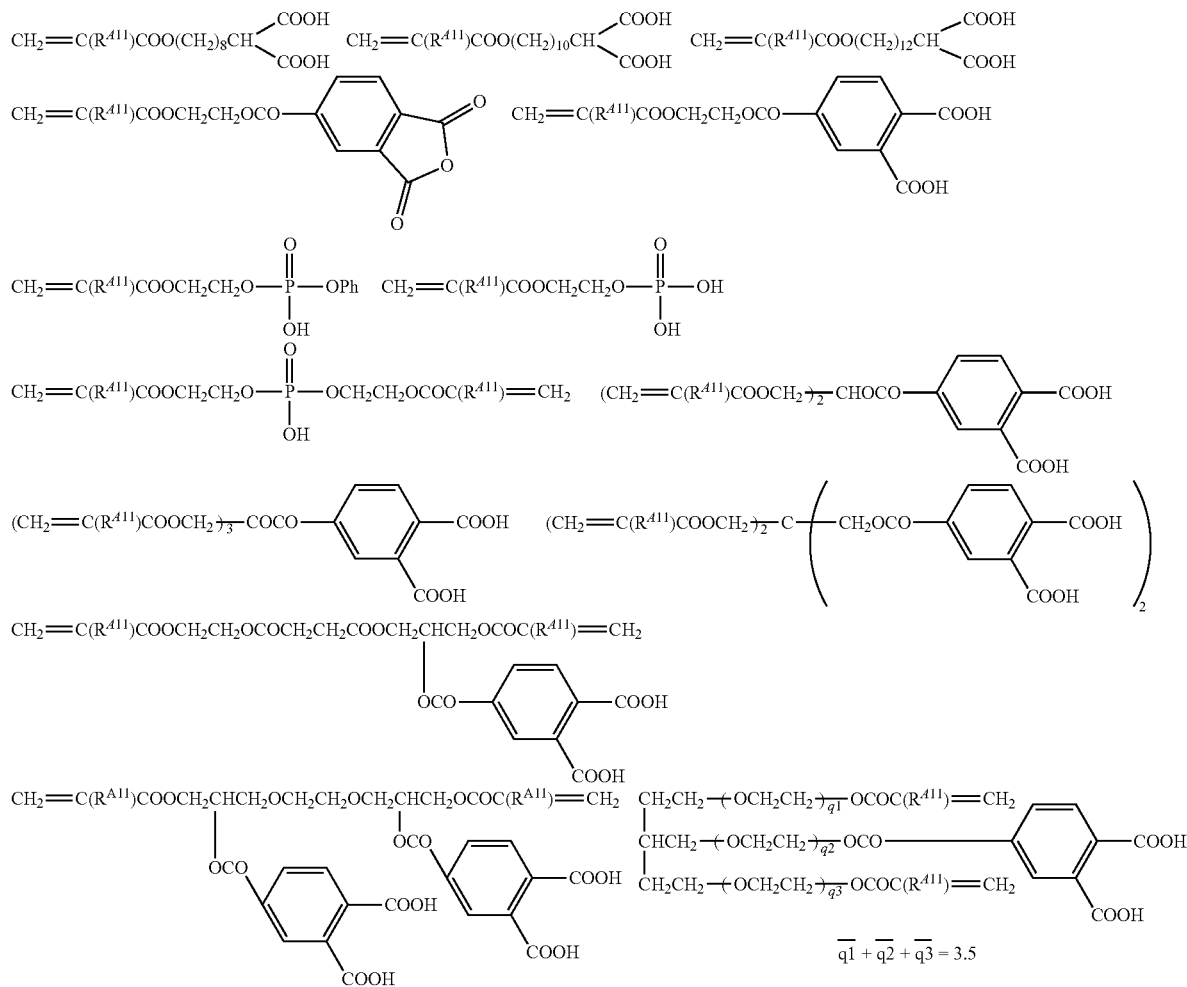

In the compound shown in the bottom row, q1, q2, and q3 each independently represent an integer of from 0 to 2. The compound is often obtained as a mixture of compounds having different values for each of q1, q2, and q3, and the average of the sums of q1, q2, and q3 in the mixture is 3.5.

-continued

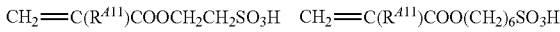

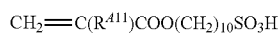

-continued $CH_2=C(R^{A11})COOC(CH_3)_2CH_2SO_3H$

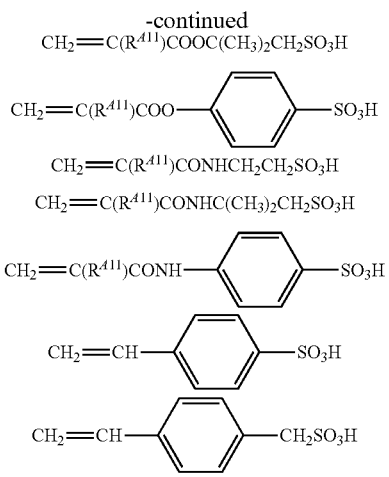

Examples of the acidic group-containing polymerizable monomer other than the acidic group-containing polymerizable monomers described above include vinyl phosphonic acids, acrylic acid, methacrylic acid, and vinylsulfonic acid.

Of the acidic group-containing polymerizable monomers exemplified above, from the standpoint of an adhesive property for a tooth substance, one having, as the acidic group, a phosphinico group $\{=P(=O)OH\}$, a phosphono group $\{-P(=O)(OH)_2\}$, a carboxyl group $\{-C(=O)OH\}$, a dihydrogen phosphate monoester group $\{-O-P(=O)(OH)_2\}$, or a hydrogen phosphate diester group $\{(-O-)_2P(=O)OH\}$ is particularly suitably used from the viewpoint of adhesive strength.

Of the acidic group-containing polymerizable monomers exemplified above, from the standpoint of an adhesive property for each of a tooth substance, a base metal, and a metal oxide, it is preferred that a long-chain phosphoric acid group-containing polymerizable monomer having a molecular structure to be described below be used as the acidic group-containing polymerizable monomer represented by the general formula (A1). That is, (ii) the hydrocarbon group or (iii) the organic residue is selected as $R^{A21}$ shown in the general formula (A1), and in this case, (ii) the hydrocarbon group is preferably a 2- to 6-valent chain hydrocarbon group having 6 to 14 carbon atoms in a main chain thereof, and (iii) the organic residue is preferably a 2- to 6-valent chain organic residue containing at least one bond selected from an ether bond and an ester bond in a main chain thereof and having 6 to 14 atoms in the main chain. In this case, a specific example of $R^{A21}$ in the long-chain phosphoric acid group-containing polymerizable monomer is an alkylene group having 6 to 14 (preferably 6 to 10) carbon atoms in a main chain thereof. In addition, $X^1$ preferably represents a dihydrogen phosphate monoester group $\{-O-P(=O)(OH)_2\}$ or a phosphono group $\{-P(=O)(OH)_2\}$.

In addition, in the two-package dental adhesive composition according to this embodiment, as the acidic group-containing polymerizable monomer, the acidic group-containing polymerizable monomer represented by the general formula (A1) may be used alone, the acidic group-containing polymerizable monomer represented by the general formula (A2) may be used alone, or the acidic group-containing polymerizable monomer represented by the general formula (A1) and the acidic group-containing polymerizable monomer represented by the general formula (A2) may be used in combination.

In order to more improve the adhesive property and adhesion durability, when the acidic group-containing polymerizable monomer represented by the general formula (A1) and the acidic group-containing polymerizable monomer represented by the general formula (A2) are used in combination, from the viewpoint of the blending ratio of the acidic group-containing polymerizable monomer, the blending ratio of the acidic group-containing polymerizable monomer represented by the general formula (A2) with respect to the total amount (100 mass %) of the acidic group-containing polymerizable monomer represented by the general formula (A1) and the acidic group-containing polymerizable monomer represented by the general formula (A2) is preferably from 3 mass % to 40 mass %, and is more preferably from 5 mass % to 30 mass %. When the blending ratio of the acidic group-containing polymerizable monomer represented by the general formula (A2) is less than 3 mass %, an adhesive property-improving effect based on an improvement in reactivity with the borate compound is not sufficiently obtained in some cases, and when the blending ratio is more than 40 mass %, adhesion durability for each of a base metal and a metal oxide is reduced in some cases.

Meanwhile, from the viewpoint of the molecular structure of the acidic group-containing polymerizable monomer, it is preferred that the above-mentioned long-chain phosphoric acid group-containing polymerizable monomer be used as the acidic group-containing polymerizable monomer represented by the general formula (A1), and a short-chain phosphoric acid group-containing polymerizable monomer having a molecular structure to be described below be used as the acidic group-containing polymerizable monomer represented by the general formula (A2). That is, (ii) the hydrocarbon group or (iii) the organic residue is independently selected as each of $R^{A21}$ and $R^{A22}$ shown in the general formula (A2), and in this case, (ii) the hydrocarbon group is preferably a 2- to 6-valent chain hydrocarbon group having 2 to 4 carbon atoms in a main chain thereof, and (iii) the organic residue is preferably a 2- to 6-valent chain organic residue containing at least one bond selected from an ether bond and an ester bond in a main chain thereof and having 2 to 4 atoms in the main chain. In this case, a specific example of each of $R^{A21}$ and $R^{A22}$ in the short-chain phosphoric acid group-containing polymerizable monomer is an alkylene group having 2 to 4 carbon atoms in a main chain thereof. In addition, $X^2$ preferably represents a hydrogen phosphate diester group $\{(-O-)_2P(=O)OH\}$ or a phosphinico group $\{=P(=O)OH\}$. When the long-chain phosphoric acid group-containing polymerizable monomer and the short-chain phosphoric acid group-containing polymerizable monomer are used in combination, reactivity between those phosphoric acid group-containing polymerizable monomers and the borate compound is improved, and hence it becomes easy to even more improve the adhesive property.

In addition, in the two-package dental adhesive composition according to this embodiment, the blending ratio of the acidic group-containing polymerizable monomer is set to preferably from 5 parts by mass to 30 parts by mass, more preferably from 10 parts by mass to 20 parts by mass with respect to 100 parts by mass of all polymerizable monomers including at least the acidic group-containing polymerizable monomer and the sulfur atom-containing polymerizable monomer. When the blending ratio is less than 5 parts by mass, sufficient adhesive strength for a tooth substance is not obtained in some cases, and when the blending ratio is more than 30 parts by mass, the adhesion durability for each of a base metal and a metal oxide is reduced in some cases.

In particular, in order to more improve the adhesion durability for each of a base metal and a metal oxide, the following blending is preferably adopted. Specifically, when (A) the acidic group-containing polymerizable monomer includes the acidic group-containing polymerizable monomer represented by the general formula (A2), the blending ratio of the acidic group-containing polymerizable monomer represented by the general formula (A2) is preferably from 1 part by mass to 10 parts by mass, more preferably from 1 part by mass to 5 parts by mass with respect to 100 parts by mass of all polymerizable monomers.

As used herein, the term "all polymerizable monomers" means all the kinds of polymerizable monomers to be used as constituent components of the two-package dental adhesive composition according to this embodiment. For example, when only (A) the acidic group-containing polymerizable monomer and (B) the sulfur atom-containing polymerizable monomer are used as polymerizable monomers, the term "all polymerizable monomers" means those two kinds of polymerizable monomers, and the amount of "all polymerizable monomers" means the total amount of the amount of (A) the acidic group-containing polymerizable monomer and the amount of (B) the sulfur atom-containing polymerizable monomer. In addition, when (G) another polymerizable monomer is further used as a constituent component of the two-package dental adhesive composition according to this embodiment in addition to (A) the acidic group-containing polymerizable monomer and (B) the sulfur atom-containing polymerizable monomer, the term "all polymerizable monomers" means those three kinds of polymerizable monomers, and the amount of "all polymerizable monomers" means the total amount of the amount of (A) the acidic group-containing polymerizable monomer, the amount of (B) the sulfur atom-containing polymerizable monomer, and the amount of (G) the other polymerizable monomer. Herein, a silane coupling agent having a polymerizable group to be described later is not classified as a "polymerizable monomer". Therefore, even when the silane coupling agent having a polymerizable group is used as a constituent component of the two-package dental adhesive composition according to this embodiment, the amount of "all polymerizable monomers" does not include the amount of the silane coupling agent having a polymerizable group.

(B) Sulfur Atom-Containing Polymerizable Monomer

The sulfur atom-containing polymerizable monomer to be blended into the first agent means a compound having, in the molecule, a sulfur atom (provided that a constituent sulfur atom of a sulfur atom-containing acidic group, such as a sulfo group, is excluded) and one or more radically polymerizable groups. Here, examples of the radically polymerizable groups include groups each containing an ethylenically unsaturated double bond, such as a methacryloyl group and a styryl group. In addition, the sulfur atom is contained in the form of not constituting an acidic group, such as a sulfo group, in the molecule, and is contained in the form of constituting a partial structure other than the acidic group by, for example, forming a partial structure, such as >C═S or >C—S—C<, in the molecule.

The sulfur atom-containing polymerizable monomer is not particularly limited as long as the sulfur atom-containing polymerizable monomer is a compound having, in the molecule, a sulfur atom (provided that a constituent sulfur atom of a sulfur atom-containing acidic group, such as a sulfo group, is excluded) and one or more radically polymerizable groups, but examples thereof include: compounds each capable of generating a mercapto group by tautomerism represented by the following general formulae (B1) to (B5); disulfide compounds represented by the following general formulae (B6) to (B9); and chain or cyclic thioether compounds represented by the following general formulae (B10) and (B11).

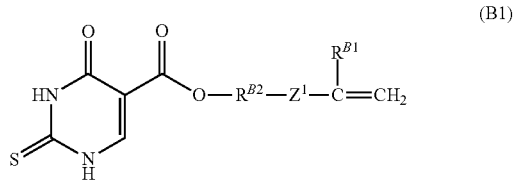
(B1)

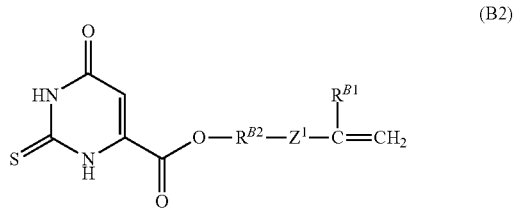
(B2)

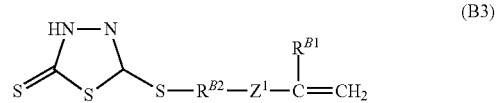
(B3)

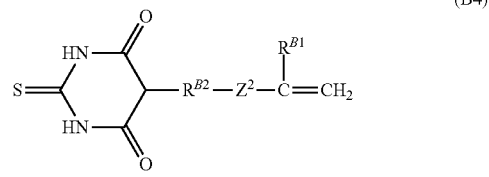
(B4)

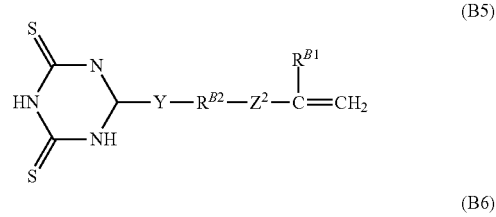
(B5)

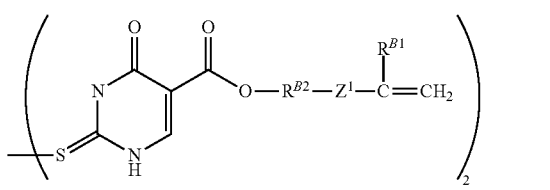
(B6)

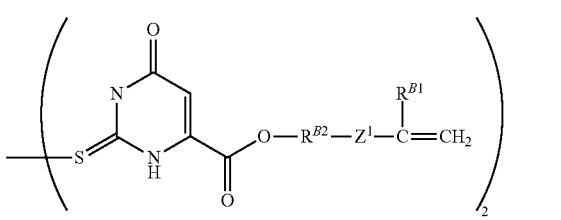
(B7)

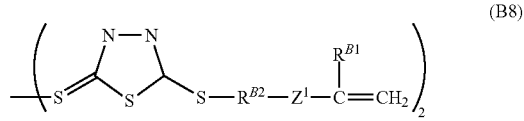
(B8)

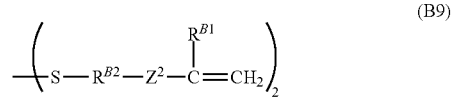
(B9)

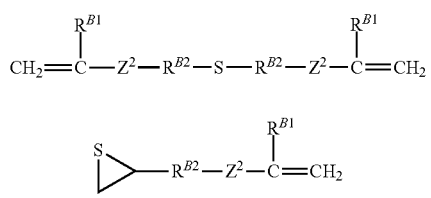

In the general formulae (B1) to (B11), $R^{B1}$ represents a hydrogen atom or a methyl group, $R^{B2}$ represents a divalent saturated hydrocarbon group having 1 to 12 carbon atoms, a —$CH_2$—$C_6H_4$—$CH_2$— group, a —$(CH_2)_o$—$Si(CH_3)_2$ $OSi(CH_3)_2$—$(CH_2)_p$— group (where o and p each represent an integer of from 1 to 5), or a —$CH_2CH_2OCH_2CH_2$— group, $Z^1$ represents a —OC(=O)— group, a —$OCH_2$— group, or a —$OCH_2$—$C_6H_4$— group (where, in each of those groups $Z^1$, the rightmost carbon atom is bonded to the carbon forming the unsaturated double bond adjacent to the group $Z^1$ and the leftmost oxygen atom is bonded to the group $R^{B2}$), $Z^2$ represents a —OC(=O)— group (where, in the group $Z^2$, the rightmost carbon atom is bonded to the carbon forming the unsaturated double bond adjacent to the group $Z^2$ and the leftmost oxygen atom is bonded to the group $R^{B2}$), a —$C_6H_4$— group, or a bonding site (where a case in which the group $Z^2$ represents a bonding site refers to a state in which the group $R^{B2}$ and the carbon forming the unsaturated double bond adjacent to the group $Z^2$ are directly bonded to each other), and Y represents —S—, —O—, or —N($R^{B3}$)— (where $R^{B3}$ represents a hydrogen atom, or an alkyl group having 1 to 5 carbon atoms).

Here, examples of the polymerizable compounds each capable of generating a mercapto group by tautomerism represented by the general formulae (B1) to (B5) include compounds shown below.

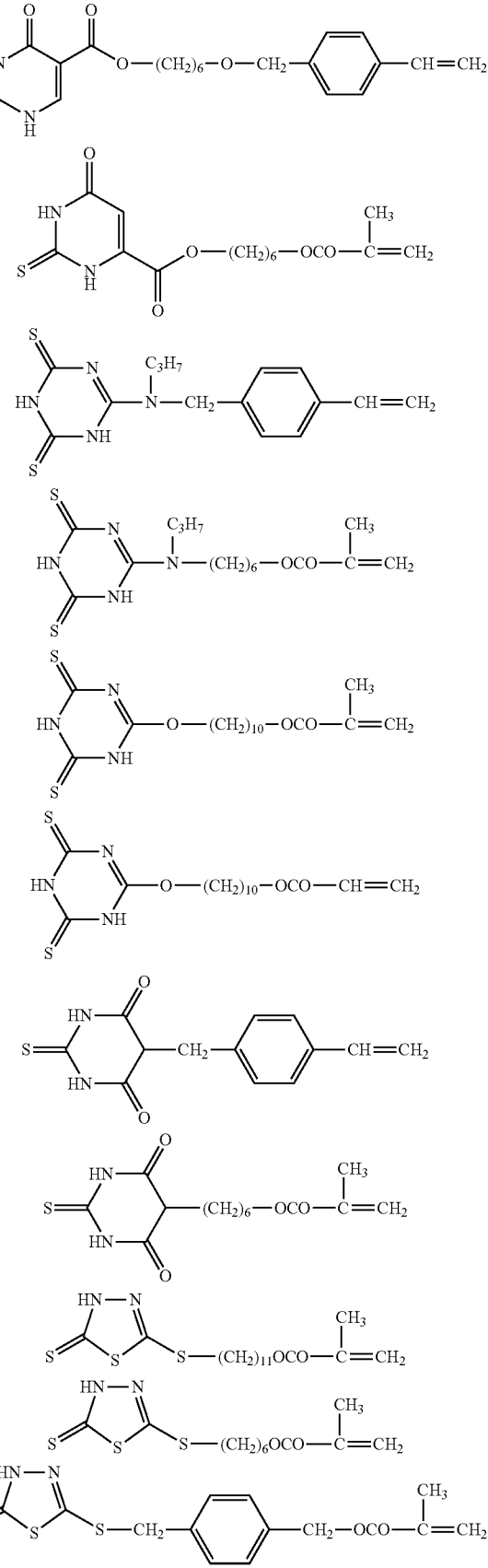

In addition, examples of the disulfide compounds represented by the general formulae (B6) to (B9) include compounds shown below.

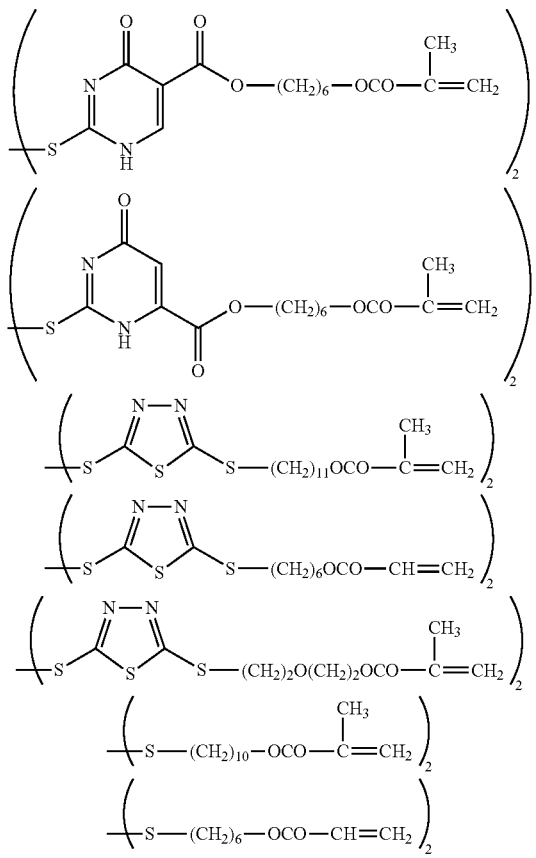

Further, examples of the chain or cyclic thioether compounds represented by the general formulae (B10) and (B11) include compounds shown below.

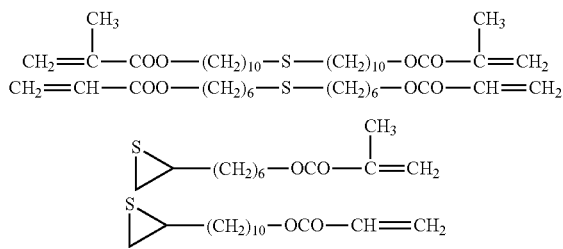

The sulfur atom-containing polymerizable monomers may be used alone or in combination thereof. In addition, from the viewpoint of the storage stability of the first agent containing the sulfur atom-containing polymerizable monomer, the sulfur atom-containing polymerizable monomer is preferably a polymerizable compound capable of generating a mercapto group by tautomerism, or a disulfide compound. Further, from the viewpoint of adhesive strength, the sulfur atom-containing polymerizable monomer is most preferably a compound capable of generating a mercapto group by tautomerism. When two or more kinds of sulfur atom-containing polymerizable monomers are used in combination, the blending ratio of the sulfur atom-containing polymerizable monomers is based on the total amount of all the kinds of sulfur atom-containing polymerizable monomers.

The blending ratio of the sulfur atom-containing polymerizable monomer is not particularly limited, but is set to preferably from 0.001 part by mass to 30 parts by mass, more preferably from 0.01 part by mass to 10 parts by mass with respect to 100 parts by mass of all polymerizable monomers. When the blending ratio is less than 0.001 part by mass, sufficient adhesive strength for a noble metal is not obtained in some cases, and when the blending ratio is more than 30 parts by mass, curability is reduced to reduce the adhesive strength in some cases.

(C) Silane Coupling Agent

As the silane coupling agent to be blended into the second agent, a known silane coupling agent may be used without any limitation, and examples thereof may include methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltris(β-methoxyethoxy)silane, γ-methacryloxypropyltrimethoxysilane, γ-methacryloxypropyltriethoxysilane, γ-methacryloxypropyltriisopropoxysilane, γ-methacryloxypropyltris(β-methoxyethoxy)silane, γ-methacryloxypropyltri(trimethylsiloxy)silane, ω-methacryloxydecyltrimethoxysilane, γ-methacryloxypropylpentamethyldisiloxane, γ-chloropropyltrimethoxysilane, γ-chloropropylmethyldimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane, γ-aminopropyltriethoxysilane, γ-(2-aminoethyl)aminopropyltrimethoxysilane, mercaptopropyltrimethoxysilane, γ-isocyanatopropyltriethoxysilane, γ-ureidopropyltriethoxysilane, and hexamethyldisilazane.

From the viewpoint of an adhesive property for each of a silica-based oxide and a composite resin material, the silane coupling agent preferably has a polymerizable group, such as a (meth)acrylic group. Further, from the viewpoint of the storage stability of the second agent containing the silane coupling agent, a compound represented by the following general formula (C1) is particularly preferably used.

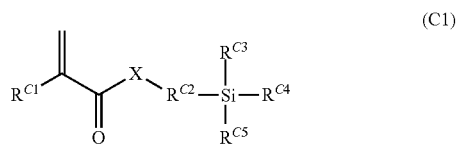

(C1)

In the general formula (C1), X represents an oxygen atom or a nitrogen atom, $R^{C1}$ represents a methyl group or a hydrogen atom, $R^{C2}$ represents an alkylene group having 1 to 10 carbon atoms, and $R^{C3}$, $R^{C4}$, and $R^{C5}$ each independently represent an alkyl group having 1 to 10 carbon atoms or an alkoxyl group having 1 to 10 carbon atoms, provided that at least one group selected from $R^{C3}$, $R^{C4}$, and $R^{C5}$ is an alkoxy group having 2 to 4 carbon atoms.

In addition, from the viewpoint of further improving the adhesive property for each of a silica-based oxide and a composite resin material, $R^{C3}$, $R^{C4}$, and $R^{C5}$ each preferably represent an alkoxy group. In addition, the number of carbon atoms of the alkoxy group is preferably from 2 to 4, most preferably 2. When the number of carbon atoms of the alkoxy group is set to 2 or more, it becomes easier to obtain excellent adhesive strength even if the second agent is stored for a long period of time before being used by being mixed with the first agent. In addition, when the number of carbon atoms of the alkoxy group is set to 4 or less, it becomes easy to more improve the adhesive strength from a time point immediately after the preparation of the second agent. Therefore, it is more preferred that $R^{C3}$, $R^{C4}$, and $R^{C5}$ each independently represent an alkoxyl group having 2 to 4 carbon atoms.

Of the silane coupling agents each represented by the general formula (C1), γ-methacryloxypropyltriethoxysilane is particularly suitable.

In addition, the above-mentioned silane coupling agents may be used alone or in combination thereof. When two or more kinds of silane coupling agents are used in combination, the blending ratio of the silane coupling agents is based on the total mass of all the kinds of silane coupling agents. When a silane coupling agent having a polymerizable group like γ-methacryloxypropyltriethoxysilane is used as the silane coupling agent, the silane coupling agent having a polymerizable group is not classified as any of the polymerizable monomers set forth in (A), (B), and (G), and is regarded as (C) the silane coupling agent in the calculation of its blending ratio.

The blending ratio of the silane coupling agent is not particularly limited, but is set to preferably from 0.1 part by mass to 30 parts by mass, more preferably from 1 part by mass to parts by mass with respect to 100 parts by mass of all polymerizable monomers. When the blending ratio is less than 0.1 part by mass, sufficient adhesive strength for each of a silica-based oxide and a composite resin material is not obtained in some cases, and when the blending ratio is more than 30 parts by mass, curability is reduced to reduce the adhesive strength in some cases.

(D) Borate Compound

As the borate compound to be blended into the second agent, any known borate compound may be used without any limitation, but an arylborate compound having an aryl group in the molecule is preferably used. An example of the arylborate compound is an arylborate compound having three or four aryl groups per molecule.

As a triarylborate compound having three aryl groups per molecule, there are given, for example, sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, and butylquinolinium salts of monoalkyltriphenylboron, monoalkyltri(p-chlorophenyl)boron, monoalkyltri(p-fluorophenyl)boron, monoalkyltri(3,5-bistrifluoromethyl)phenylboron, monoalkyltri[3,5-bis(1,1,1,3,3,3-hexafluoro-2-methoxy-2-propyl) phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl) boron (the alkyl group is, for example, a n-butyl group, a n-octyl group, a n-dodecyl group or the like).

In addition, as a tetraarylborate compound having four aryl groups per molecule, there are given, for example, sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, and butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis (m-butylphenyl)boron, tetrakis(p-butyloxyphenyl)boron, tetrakis(m-butyloxyphenyl)boron, tetrakis(p-octyloxyphenyl)boron, and tetrakis(m-octyloxyphenyl)boron (the alkyl group is, for example, a n-butyl group, a n-octyl group, a n-dodecyl group, or the like).

Of the arylborate compounds listed above, from the viewpoint of the storage stability of the second agent, a tetraarylborate compound is preferred, and an alkali metal salt of a tetraarylborate is still more preferred.

The borate compounds may be used alone or in combination thereof. When two or more kinds thereof are used in combination, the blending ratio of the borate compounds is based on the total mass of all the kinds of borate compounds.

As described above, the borate compound has a function as a polymerization accelerator. Examples of the polymerization accelerator include, in addition to the borate compounds, (a) organic peroxides, such as benzoyl peroxide, (b) azo compounds, such as azobisbutyronitrile, (c) sulfinates, such as sodium benzenesulfinate, (d) amines (secondary amines, such as N-methylaniline, and tertiary amines, such as triethylamine), (e) α-diketones, such as camphorquinone, (f) thioxanthones, such as 2,4-diethylthioxanthone, (g) α-aminoacetophenones, such as 2-benzyl-diethylamino-1-(4-morpholinophenyl)-pentanone-1, (h) acylphosphine oxides, such as bis(2,6-dimethoxybenzoyl)-2,4,4-trimethylpentylphosphine oxide, (i) barbituric acids, such as 5-butylbarbituric acid, (j) colorants, such as 3-thienoylcoumarin, (k) photoacid generators, such as 2,4,6-tris(trichloromethyl)-s-triazine, (l) organic borons, such as triphenylborane, tributylborane, and tributylborane oxide, and (m) transition metal compounds, such as iron chloride, copper chloride, iron nitrate, and iron citrate.

However, as a result of trial and error performed by the inventors of the present invention, a two-package composition obtained by combining a polymerization accelerator other than the borate compound in place of the borate compound with the components set forth in (A) to (C) and (E) was insufficient in adhesive property for at least any one adherend selected from a tooth substance, a base metal, a noble metal, a metal oxide, a silica-based oxide, and a composite resin material, or, in the case of using any of the polymerization accelerators set forth in the (a) to (m) in place of the borate compound, it was impossible to simultaneously sufficiently achieve both an adhesive property and storage stability even when the combination of the components to be respectively blended into the first agent and the second agent was variously changed. However, in the two-package dental adhesive composition according to this embodiment, the polymerization accelerators set forth in the (a) to (m) may be used in combination with the borate compound as required for the purpose of, for example, further improving the adhesive property.

The blending ratio of the borate compound is not particularly limited, but is set to preferably from 0.1 part by mass to 15 parts by mass, more preferably from 1 part by mass to parts by mass with respect to 100 parts by mass of all polymerizable monomers. When the blending ratio is less than 0.1 part by mass, a polymerization and curing reaction is not sufficiently accelerated, and adhesive strength particularly for dentin is reduced in some cases, and when the blending ratio is more than 15 parts by mass, a compound amount after the reaction of the borate compound having no polymerizability is increased, and hence curability is reduced to reduce the adhesive strength in some cases.

(E) Water

The water to be blended into the second agent is preferably substantially free of harmful impurities from the viewpoints of storage stability, biocompatibility, and an adhesive property, and for example, deionized water, distilled water, or the like may be utilized.

The blending ratio of the water is set to preferably from 5 parts by mass to 50 parts by mass, more preferably from 10 parts by mass to 40 parts by mass with respect to 100 parts by mass of polymerization-reactive components. When the blending ratio is less than 5 parts by mass, sufficient adhesive strength for each of a tooth substance, a silica-based oxide, and a composite resin material is not obtained in some cases. Meanwhile, when the blending ratio is more than 50 parts by mass, water is liable to remain after air blowing, and the adhesive strength is reduced in some cases. Further, the storage stability of the silane coupling agent is reduced, and the adhesive strength particularly for a silica-based oxide is reduced in some cases.

Herein, the "polymerization-reactive components" are components each exhibiting an adhesive property for a tooth substance and a material for restoration (such as a prosthesis or a composite resin), and include at least: (A) the acidic group-containing polymerizable monomer and (B) the sulfur atom-containing polymerizable monomer, which are essential constituent components of the first agent; and (C) the silane coupling agent, which is an essential constituent component of the second agent. In addition, when at least one of the first agent or the second agent contains (G) a polymerizable monomer other than (A) the acidic group-containing polymerizable monomer and (B) the sulfur atom-containing polymerizable monomer, (G) the other polymerizable monomer is also included in the "polymerization-reactive components".

Suitable blending ratios of (C) the silane coupling agent, (D) the borate compound, and (E) the water in the second agent are not particularly limited, but the following blending ratios are preferably satisfied. That is, the blending ratio of (D) the borate compound with respect to 100 parts by mass of (C) the silane coupling agent is preferably from 1 part by mass to 300 parts by mass, more preferably from 10 parts by mass to 200 parts by mass, still more preferably from 10 parts by mass to 150 parts by mass. When the blending ratio of (D) the borate compound is set to from 1 part by mass to 300 parts by mass, the storage stability of the second agent itself, in particular, the storage stability of the silane coupling agent can be more improved. In addition, from a similar viewpoint, the blending ratio of (E) the water with respect to 100 parts by mass of (C) the silane coupling agent is preferably from 20 parts by mass to 1,500 parts by mass, more preferably from 25 parts by mass to 1,250 parts by mass, still more preferably from 100 parts by mass to 850 parts by mass.

(F) Organic Solvent

An organic solvent may be further added, as required, to at least one of the first agent or second agent included in the two-package dental adhesive composition according to this embodiment. As the organic solvent, any known organic solvent may be used without any limitation, but it is generally preferred to use a highly volatile organic solvent having a boiling point of less than 100° C.

Examples of such organic solvent include: alcohols, such as methanol, ethanol, isopropyl alcohol, and butanol; ketones, such as acetone and methyl ethyl ketone; ethers, such as ethyl ether, 1,4-dioxane, and tetrahydrofuran; esters, such as ethyl acetate and ethyl formate; aromatic solvents, such as toluene, xylene, and benzene; hydrocarbon-based solvents, such as pentane, hexane, heptane, and octane; chlorine-based solvents, such as methylene chloride, chloroform, and 1,2-dichloroethane; and fluorine-based solvents, such as trifluoroethanol. Of those, for reasons such as solubility and storage stability, acetone, toluene, ethanol, isopropyl alcohol, or the like is particularly preferably used. The organic solvents may be used alone or in combination thereof. When two or more kinds thereof are used in combination, the blending ratio of the organic solvents is based on the total mass of all the kinds of organic solvents.

The organic solvent may be added to only the first agent, may be added to only the second agent, or may be added to both of the first agent and the second agent. In addition, (a) as the organic solvent to be added to the first agent, one kind of organic solvent may be used alone, or two or more kinds of organic solvents may be used in combination. The same applies to the second agent. In addition, (b) when the organic solvent is added to each of the first agent and the second agent, the organic solvent to be used for the first agent and the organic solvent to be used for the second agent may be identical to or different from each other.

In addition, as the organic solvent to be used, it is preferred to use at least an organic solvent having a boiling point of from 50° C. to 65° C. at normal pressure (1 atm) (hereinafter sometimes referred to as "low-boiling-point organic solvent") and an organic solvent having a boiling point of from 75° C. to 90° C. at normal pressure (1 atm) (hereinafter sometimes referred to as "high-boiling-point organic solvent"). In this case, with respect to 100 parts by mass of the polymerization-reactive components including at least (A) the acidic group-containing polymerizable monomer, (B) the sulfur atom-containing polymerizable monomer, and (C) the silane coupling agent, it is preferred to use 200 parts by mass to 400 parts by mass of the low-boiling-point organic solvent and 25 parts by mass to 120 parts by mass of the high-boiling-point organic solvent.

When the blending amounts of the low-boiling-point organic solvent and the high-boiling-point organic solvent with respect to 100 parts by mass of the polymerization-reactive components are set to fall within the above-mentioned ranges, in the bonding of a prosthesis made of a metal, ceramics, a hybrid resin, CAD/CAM resin block, or the like to a tooth substance through the use of the two-package dental adhesive composition according to this embodiment in combination with dental resin cement, it becomes easy to suppress the bonding of the prosthesis in a floating state.

Each of the low-boiling-point organic solvent and the high-boiling-point organic solvent may be added to only any one of the first agent and the second agent, or may be added to both thereof. Of course, the low-boiling-point organic solvents and the high-boiling-point organic solvents may be used alone or in combination thereof. When two or more kinds thereof are used in combination, the blending ratio of the low-boiling-point organic solvents and that of the high-boiling-point organic solvents are based on the total mass of the respective organic solvents.

The low-boiling-point organic solvent may be appropriately selected from known organic solvents as long as the boiling point at normal pressure (1 atm) falls within the range of from 50° C. to 65° C. in consideration of, for example, the solubility of other constituent components of the two-package dental adhesive composition. Examples of such organic solvent may include acetone (boiling point: 56.5° C.), methanol (boiling point: 64.7° C.), ethyl formate (boiling point: 54.3° C.), and chloroform (boiling point: 61.2° C.). The low-boiling-point organic solvents may be used alone or in combination thereof.

The high-boiling-point organic solvent may be appropriately selected from known organic solvents as long as the boiling point at normal pressure (1 atm) falls within the range of from 75° C. to 90° C. in consideration of, for example, the solubility of other constituent components of the two-package dental adhesive composition. Examples of such organic solvent may include isopropyl alcohol (IPA, boiling point: 82.6° C.), ethanol (boiling point: 78.4° C.), methyl ethyl ketone (boiling point: 79.5° C.), benzene (boiling point: 80.1° C.), ethyl acetate (boiling point: 77.1° C.), 1,2-dichloroethane (boiling point: 83.5° C. to 84° C.), trifluoroethanol (boiling point: 78° C.), and 2-methylhexane (boiling point: 90° C.). The high-boiling-point organic solvents may be used alone or in combination thereof.

The low-boiling-point organic solvent and the high-boiling-point organic solvent may be appropriately selected from the known organic solvents having predetermined boiling points as exemplified above, and used in combination. From the viewpoint of, for example, the solubility of other constituent components of the two-package dental adhesive composition, it is particularly preferred to use acetone and isopropyl alcohol in combination.

In addition, as required, another organic solvent whose boiling point at normal pressure (1 atm) falls outside the ranges of from 50° C. to 65° C. and from 75° C. to 90° C. may also be used. With regard to the blending amount of the other organic solvent, an appropriate amount thereof may be used within a range in which the securement of a moderate operation time and the suppression of floating of a prosthesis at the time of the bonding of the prosthesis are not adversely affected. For example, the blending amount is set to preferably 50 parts by mass or less, more preferably 30 parts by mass or less, still more preferably 10 parts by mass or less with respect to 100 parts by mass of the polymerization-reactive components, or the other organic solvent may not be used at all. Examples of the other organic solvent may include pentane (boiling point: 36.1° C.), methylene chloride (boiling point: 39.6° C.), diethyl ether (boiling point: 34.6° C.), tetrahydrofuran (boiling point: 66° C.), hexane (boiling point: 68° C.), heptane (boiling point: 98.4° C.), 1,4-dioxane (boiling point: 101° C.), and toluene (boiling point: 110.6° C.)

A difference ΔT between the boiling points of the low-boiling-point organic solvent and the high-boiling-point organic solvent to be used for the two-package dental adhesive composition according to this embodiment (=boiling point of high-boiling-point organic solvent−boiling point of low-boiling-point organic solvent) may be appropriately selected within the range of from 10° C. to 40° C. From the viewpoint of achieving both the suppression of floating of a prosthesis and the securement of a sufficient operation time in a more balanced manner, the difference ΔT between the boiling points is preferably from 13° C. to 34° C.

In addition, when the organic solvent is blended into the first agent or the second agent, an adjustment is preferably made so that the following ratio may be satisfied in each agent. That is, when the organic solvent is added to the first agent, the content of the organic solvent in the first agent falls within the range of preferably from 30 mass % to 90 mass %, more preferably from 50 mass % to 70 mass %. Similarly, when the organic solvent is added to the second agent, the content of the organic solvent in the second agent falls within the range of preferably from 10 mass % to 99 mass %, more preferably from 30 mass % to 90 mass %. When the content of the organic solvent in each of the first agent and the second agent is set to fall within the above-mentioned range, it becomes easy to improve storage stability in each agent, and to mix the first agent and the second agent with each other and control the thickness of a coating formed of the two-package dental adhesive composition according to this embodiment applied to a bonding surface.

Further, when the first agent and the second agent each further contain the organic solvent, the ratio of the total amount of the organic solvent to the total amount of the first agent and the second agent is preferably from 63 mass % to 85 mass %, particularly preferably from 65 mass % to 80 mass %. When the ratio of the total amount of the organic solvent to the total amount of the first agent and the second agent is less than 63 mass %, a sufficient operation time cannot be secured in some cases depending on the progress of chemical polymerization after the mixing between the first agent and the second agent. When the ratio of the total amount of the organic solvent to the total amount of the first agent and the second agent is more than 85 mass %, the thickness of the coating formed of the two-package dental adhesive composition according to this embodiment applied to the bonding surface is reduced to reduce the adhesive property in some cases. Further, when the ratio of the total amount of the organic solvent to the total amount of the first agent and the second agent is set to fall within the above-mentioned range, the mixing between the first agent and the second agent is facilitated.

(G) Other Polymerizable Monomer (G) The polymerizable monomer other than (A) the acidic group-containing polymerizable monomer and (B) the sulfur atom-containing polymerizable monomer is suitably further used for the two-package dental adhesive composition according to this embodiment from the viewpoint of an adhesive property and adhesion durability for a tooth substance.

As the other polymerizable monomer, a known compound may be used without any particular limitation as long as the compound does not contain an acidic group and a sulfur atom (provided that a constituent sulfur atom of a sulfur atom-containing acidic group, such as a sulfo group, is excluded) in the molecule and contains one or more polymerizable unsaturated groups therein. Here, examples of the polymerizable unsaturated groups include the same examples as those of the polymerizable unsaturated groups contained in the acidic group-containing polymerizable monomer. From the viewpoint of an adhesive property, an acryloyl group, a methacryloyl group, an acrylamide group, a methacrylamide group, or the like is preferred.

Suitable specific examples of the other polymerizable monomer may include: monofunctional polymerizable monomers, such as methyl (meth)acrylate, ethyl (meth)acrylate, butyl (meth)acrylate, glycidyl (meth)acrylate, 2-cyanomethyl (meth)acrylate, benzyl methacrylate, polyethylene glycol mono(meth)acrylate, allyl (meth)acrylate, 2-hydroxyethyl (meth)acrylate, 3-hydroxypropyl (meth)acrylate, and glyceryl mono(meth)acrylate; polyfunctional polymerizable monomers, such as ethylene glycol di(meth)acrylate, diethylene glycol di(meth)acrylate, triethylene glycol di(meth)acrylate, nonaethylene glycol di(meth)acrylate, propylene glycol di(meth)acrylate, dipropylene glycol di(meth)acrylate, 2,2'-bis[4-(meth)acryloyloxyethoxyphenyl]propane, 2,2'-bis[4-(meth)acryloyloxyethoxyethoxyphenyl]propane, 2,2'-bis[4-(meth)acryloyloxyethoxyethoxyethoxyethoxyphenyl]propane, 2,2'-bis{4-[2-hydroxy-3-(meth)acryloyloxypropoxy]phenyl}propane, 1,4-butanediol di(meth)acrylate, 1,6-hexanediol di(meth) acrylate, 1,9-nonanediol di(meth)acrylate, trimethylolpropane tri(meth)acrylate, neopentyl glycol di(meth)acrylate, 1,6-bis(methacrylethyloxycarbonylamino)-2,2,4-trimethylhexane, 1,6-bis(methacrylethyloxycarbonylamino)-2,4,4-trimethylhexane, urethane (meth)acrylate, epoxy (meth) acrylate, trimethylolpropane trimethacrylate, and pentaerythritol tetramethacrylate; fumaric acid ester compounds, such as monomethyl fumarate, diethyl fumarate, and diphenyl fumarate; styrene and α-methylstyrene derivatives, such as styrene, divinylbenzene, α-methylstyrene, and α-methylstyrene dimer; and allyl compounds, such as diallyl phthalate, diallyl terephthalate, diallyl carbonate, and allyl diglycol carbonate.

Of the above-mentioned other polymerizable monomers, a polyfunctional polymerizable monomer is suitably used from the viewpoint of an adhesive property and adhesion durability for a tooth substance. Specific examples of the polyfunctional polymerizable monomer that is suitably used include 2,2'-bis{4-[2-hydroxy-3-(meth)acryloyloxypropoxy]phenyl}propane, triethylene glycol methacrylate, 2,2-bis[(4-(meth)acryloyloxypolyethoxyphenyl)propane], 1,6-bis(methacrylethyloxycarbonylamino)-2,2,4-trimethylhexane, 1,6-bis(methacrylethyloxycarbonylamino)-2,4,4-trimethylhexane, and trimethylolpropane trimethacrylate.

The other polymerizable monomers may be used alone or in combination thereof. When two or more kinds thereof are used in combination, the blending ratio of the other polymerizable monomers is based on the total mass of all polymerizable monomers. In addition, (G) the other polymerizable monomer may be added to any one or both of the first agent and the second agent, but is generally preferably added to only the first agent.

The blending ratio of the other polymerizable monomer is not particularly limited, but is an amount excluding (A) the acidic group-containing polymerizable monomer and (B) the sulfur atom-containing polymerizable monomer with respect to 100 parts by mass of all polymerizable monomers. From the viewpoint of sufficiently securing also an adhesive property-improving effect derived from the acidic group-containing polymerizable monomer and the sulfur atom-containing polymerizable monomer, the blending ratio of the other polymerizable monomer is set to preferably from 40 parts by mass to 95 parts by mass, more preferably from 70 parts by mass to 90 parts by mass with respect to 100 parts by mass of all polymerizable monomers.

(H) Organic Peroxide and (I) Decomposition Accelerator

It is also suitable that an organic peroxide and its decomposition accelerator be added to the two-package dental adhesive composition according to this embodiment as required, for the purpose of further improving polymerization activity. In this case, it becomes easier to improve adhesive strength particularly for dentin.

As the organic peroxide, a known compound may be used without any limitation, and there are typically used, for example, a ketone peroxide, a peroxyketal, a hydroperoxide, a diaryl peroxide, a peroxyester, a diacyl peroxide, and a peroxydicarbonate. Specific examples of those organic peroxides include the following.

Here, examples of the ketone peroxide include methyl ethyl ketone peroxide, cyclohexanone peroxide, methylcyclohexanone peroxide, methyl acetoacetate peroxide, and acetylacetone peroxide.

Examples of the peroxyketal include 1,1-bis(t-hexylperoxy)3,3,5-trimethylcyclohexane, 1,1-bis(t-hexylperoxy)cyclohexane, 1,1-bis(t-butylperoxy)3,3,5-trimethylcyclohexane, 1,1-bis(t-butylperoxy)cyclohexane, 1,1-bis(t-butylperoxy)cyclododecane, 2,2-bis(t-butylperoxy)butane, n-butyl 4,4-bis(t-butylperoxy)valerate, and 2,2-bis(4,4-di-t-butylperoxycyclohexyl)propane.

Examples of the hydroperoxide include P-menthane hydroperoxide, diisopropylbenzene hydroperoxide, 1,1,3,3-tetramethylbutyl hydroperoxide, cumene hydroperoxide, t-hexyl hydroperoxide, and t-butyl hydroperoxide. Examples of the dialkyl peroxide include α,α-bis(t-butylperoxy)diisopropylbenzene, dicumyl peroxide, 2,5-dimethyl-2,5-bis(t-butylperoxy)hexane, t-butyl cumyl peroxide, di-t-butyl peroxide, and 2,5-dimethyl-2,5-bis(t-butylperoxy) hexyne-3.

Examples of the diacyl peroxide include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, and benzoyl peroxide.

Examples of the peroxydicarbonate include di-n-propyl peroxydicarbonate, diisopropyl peroxydicarbonate, bis(4-t-butylcyclohexyl) peroxydicarbonate, di-2-ethoxyethyl peroxydicarbonate, di-2-ethylhexylperoxydicarbonate, di-2-methoxybutyl peroxydicarbonate, and di(3-methyl-3-methoxybutyl) peroxydicarbonate.

Examples of the peroxyester include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanoate, 2,5-dimethyl-2,5-bis(2-ethylhexanoylperoxy)hexane, 1-cyclohexyl-1-methylethyl peroxy-2-ethylhexanoate, t-hexyl peroxy-2-ethylhexanoate, t-butyl peroxy-2-ethylhexanoate, t-butyl peroxyisobutyrate, t-hexyl peroxyisopropyl monocarbonate, t-butyl peroxymaleic acid, t-butyl peroxy-3,5,5-trimethylhexanoate, t-butyl peroxylaurate, 2,5-dimethyl-2,5-bis(m-toluoylperoxy) hexane, t-butyl peroxyisopropyl monocarbonate, t-butyl peroxy-2-ethylhexyl monocarbonate, t-hexyl peroxybenzoate, 2,5-dimethyl-2,5-bis(benzoylperoxy)hexane, t-butylperoxyacetate, t-butyl peroxy-m-toluoyl benzoate, t-butyl peroxybenzoate, and bis(t-butylperoxy)isophthalate.

In addition to those compounds, for example, t-butyl trimethylsilyl peroxide and 3,3',4,4'-tetra(t-butylperoxycarbonyl)benzophenone may be suitably used. Those organic peroxides may be used alone or in combination thereof, and from the standpoint of polymerization activity, a hydroperoxide is particularly preferably used.

In addition, from the viewpoint of further improving polymerization activity, it is still more preferred that a decomposition accelerator for accelerating the decomposition of the organic peroxide be used in combination with the organic peroxide. The decomposition accelerator is not particularly limited as long as the decomposition accelerator is a compound having an action of accelerating the decomposition of the organic peroxide in the coexistence of the borate compound, but a metal compound selected from the group consisting of vanadium compounds, iron compounds, copper compounds, molybdenum compounds, manganese compounds, cobalt compounds, and tungsten compounds exemplified below is particularly preferably used.

Here, specific examples of the metal compound include: vanadium compounds, such as vanadium(V) oxide, vanadium oxide acetylacetonate, sodium vanadate, and vanadium oxytrichloride; iron compounds, such as iron(III) chloride, iron(III) acetylacetonate, iron(III) naphthenate, and iron(III) citrate; copper compounds, such as copper(II) chloride, copper(II) citrate, copper(II) acetylacetonate, and copper(II) stearate; molybdenum compounds, such as molybdenum (VI) oxide and molybdenum oxide acetylacetonate; manganese compounds, such as manganese(IV) oxide and manganese naphthenate; cobalt compounds, such as cobalt naphthenate and cobalt(III) acetylacetonate; and tungsten compounds, such as tungsten(VI) oxide, sodium tungstate, and tungstosilicic acid.

From the viewpoint of storage stability, the organic peroxide is preferably added to the second agent. The reason for this is as follows: when the organic peroxide is added to the first agent, the organic peroxide and (B) the sulfur atom-containing polymerizable monomer react with each other to cause gelation during storage, and hence the storage stability of the first agent is reduced. Further, when the decomposition accelerator is also used in combination, the decomposition accelerator is preferably added to the first agent in order to suppress the decomposition of the organic peroxide during storage.

The blending amount of the organic peroxide is not particularly limited, but from the viewpoint of polymerization activity, is preferably from 0.1 mol to 10 mol, more preferably from 0.5 mol to 5 mol with respect to 1 mol of the borate compound. In addition, the use amount of the decomposition accelerator is not particularly limited, but from the viewpoint of polymerization activity, is preferably from 0.001 mol to 1 mol, more preferably from 0.05 mol to 0.1 mol with respect to 1 mol of the organic peroxide.

(J) Coating Reinforcing Agent

When bonding is performed using the two-package dental adhesive composition according to this embodiment, a coating formed of a mixed composition obtained by mixing the first agent and the second agent is formed on the surface of a first adherend, and the first adherend and a second adherend are bonded to each other through the intermediation of the coating. In addition, the bonding between the first adherend and the second adherend is generally carried out at a stage before the completion of the curing of the coating, which is cured by chemical polymerization. Accordingly, when the strength of the coating at the time of the bonding is low, the coating is crushed between the adherends to become extremely thin at the time of the bonding, and hence the adhesive strength is significantly reduced in some cases. Therefore, a coating reinforcing agent may be used in order to suppress such variation in adhesive strength and make it easy to secure high adhesive strength always and stably at the time of the bonding.

The coating reinforcing agent is not particularly limited as long as the coating reinforcing agent is a substance capable of improving the strength of the coating in an uncured state at the time of bonding work. For example, there may be used: a resin material, such as a polymethyl methacrylate (PMMA) resin; an inorganic filler, such as silica particles, silica-zirconia particles, quartz, or fluoroaluminosilicate glass; particles (organic filler) formed of an organic polymer, such as polymethyl methacrylate, a polymethyl methacrylate-polyethyl methacrylate copolymer, an ethylene-vinyl acetate copolymer, or a styrene-butadiene copolymer; or a granular organic-inorganic composite filler obtained by mixing the above-mentioned inorganic particles with a polymerizable monomer, followed by polymerization and pulverization. The coating reinforcing agents may be used alone or in combination thereof. When two or more kinds thereof are used in combination, the blending ratio of the coating reinforcing agents is based on the total mass of all the kinds of coating reinforcing agents.

The coating reinforcing agent may be added to at least any one or both of the first agent and the second agent. However, from the viewpoint of storage stability, a silica-based inorganic filler, which has a risk of reacting with the silane coupling agent, is preferably added to the first agent.

The coating reinforcing agent may be used within a range in which the adhesive property and storage stability of the two-package dental adhesive composition according to this embodiment are not adversely affected in a remarkable manner. Therefore, when the coating reinforcing agent is used, preferably 0.1 part by mass to 100 parts by mass, more preferably 1 part by mass to 50 parts by mass of the coating reinforcing agent is used with respect to 100 parts by mass of all polymerizable monomers.

(K) Other Additive

In addition, an additive other than those described above may be further used for the two-package dental adhesive composition according to this embodiment as required. Examples of such additive may include: a colorant; a photopolymerization initiator; and a polymerization inhibitor, such as hydroquinone monomethyl ether, hydroquinone, or 4-tert-butylphenol. When the photopolymerization initiator is used, the two-package dental adhesive composition according to this embodiment can be bonded or cured by photoirradiation as well.

As the photopolymerization initiator, a known photopolymerization initiator may be used without any limitation, and examples thereof include photopolymerization initiators such as: a combination of an α-diketone and a tertiary amine; a combination of an acylphosphine oxide and a tertiary amine; a combination of a thioxanthone and a tertiary amine; and a combination of an α-aminoacetophenone and a tertiary amine.

Examples of the α-diketone include camphorquinone, benzil, α-naphthyl, acetonaphthene, naphthoquinone, p,p'-dimethoxybenzil, p,p'-dichlorobenzylacetyl, 1,2-phenanthrenequinone, 1,4-phenanthrenequinone, 3,4-phenanthrenequinone, and 9,10-phenanthrenequinone.

Examples of the tertiary amine include N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, N,N-dimethylanthranilic acid methyl ester, N,N-dihydroxyethylaniline, N,N-dihydroxyethyl-p-toluidine, p-dimethylaminophenethyl alcohol, p-dimethylaminostilbene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol. Those tertiary amines may be used alone or in combination thereof.

Examples of the acylphosphine oxide include benzoyl diphenylphosphine oxide, 2,4,6-trimethylbenzoyl diphenylphosphine oxide, 2,6-dimethoxybenzoyl diphenylphosphine oxide, 2,6-dichlorobenzoyl diphenylphosphine oxide, and 2,3,5,6-tetramethylbenzoyl diphenylphosphine oxide.

Examples of the thioxanthone include 2-chlorothioxanthone and 2,4-diethylthioxanthone.

Examples of the α-aminoacetophenone include 2-benzyl-dimethylamino-1-(4-morpholinophenyl)-butanone-1, 2-benzyl-diethylamino-1-(4-morpholinophenyl)-butanone-1, 2-benzyl-dimethylamino-1-(4-morpholinophenyl)-propanone-1, 2-benzyl-diethylamino-1-(4-morpholinophenyl)-propanone-1, 2-benzyl-dimethylamino-1-(4-morpholinophenyl)-pentanone-1, and 2-benzyl-diethylamino-1-(4-morpholinophenyl)-pentanone-1.

The above-mentioned photopolymerization initiators may be used alone or as a mixture thereof. When two or more kinds thereof are used in combination, the blending ratio of the photopolymerization initiators is based on the total mass of all the kinds of photopolymerization initiators. When the photopolymerization initiator is used, it is preferred that the photopolymerization initiator be used in an effective amount within a range in which the adhesive property and storage stability of the two-package dental adhesive composition according to this embodiment are not adversely affected in a remarkable manner. Specifically, the amount of the photopolymerization initiator is set to preferably from 0.01 part by mass to 10 parts by mass, more preferably from 0.1 part by mass to 8 parts by mass with respect to 100 parts by mass of all polymerizable monomers.

When the two-package dental adhesive composition according to this embodiment is used for aesthetic treatment, the mixture of the first agent and the second agent is generally liable to be colored owing to the color of a photopolymerization-type initiator itself. In this case, it is preferred that the photopolymerization-type initiator be not added to the two-package dental adhesive composition according to this embodiment. In addition, also when it is desired to lengthen an operation time under ambient light after the two-package dental adhesive composition according to this embodiment has been collected in a mixing dish, it is preferred that the photopolymerization-type initiator be not added to the two-package dental adhesive composition according to this embodiment.

EXAMPLE OF PREFERRED EMBODIMENT

The two-package dental adhesive composition according to this embodiment is excellent in adhesive property for each of various dental materials. However, when the two-package dental adhesive composition according to this embodiment further includes an organic solvent, even if the composition is identical except for the solvent components (organic solvent and water) included in the two-package dental adhesive composition, the adhesive property may be slightly reduced, though an excellent adhesive property is still secured, depending on differences in kinds or blending amounts of the solvent components. In addition, when a tooth is restored using a prosthesis, the prosthesis may be bonded in a floating state with respect to a tooth substance depending on the differences in kinds or blending amounts of the solvent components.

Therefore, in order to more improve the adhesive property easily, and prevent the prosthesis from being bonded in a floating state with respect to the tooth substance in the restoration of a tooth using the prosthesis, the two-package dental composition according to this embodiment is particularly preferably a composition that uses 200 parts by mass to 400 parts by mass of the low-boiling-point organic solvent and 25 parts by mass to 120 parts by mass of the high-boiling-point organic solvent with respect to 100 parts by mass of the polymerization-reactive components. Such composition is hereinafter sometimes referred to as "first composition", and a composition that does not satisfy the conditions of the first composition regarding the combination and blending amounts of the two kinds of organic solvents described above is hereinafter sometimes referred to as "second composition".

That is, as compared to the second composition, the first composition allows the adhesive property to be further improved more easily, and moreover, can more reliably prevent the prosthesis from being bonded in a floating state with respect to the tooth substance in the restoration of a tooth using the prosthesis. The inventors of the present invention presume that the reason why such effects are obtained is as described below. Here, in finding the above-mentioned effects, first, the inventors of the present invention investigated related-art dental adhesive compositions regarding the cause of adhesion failure in actual dental treatment occurring even when an excellent adhesive property can be expected according to experimental data.

First, many of even the related-art dental adhesive compositions show an excellent adhesive property according to experimental data. On the other hand, however, even when dental treatment is carried out in a mouth using any of the related-art dental adhesive compositions, adhesion failure occurs or the prosthesis floats in the bonding of the prosthesis to the tooth substance in many cases. In this regard, the inventors of the present invention suspected that, hitherto, the environment in the mouth had not been sufficiently reproduced in the evaluation of an adhesive property or the like. That is, in the generally often performed evaluation of an adhesive property or the like outside the mouth, bonding work itself is carried out in a normal-temperature environment (about 20° C. to about 25° C.), but the temperature environment at the time of actual bonding is the temperature in the mouth (about 37° C.). From this fact, it is considered that, in the related-art evaluation of an adhesive property or the like outside the mouth, the environment in the mouth is not sufficiently reproduced regarding the volatilization rate of a solvent contained in the dental adhesive composition and the rate of curing with chemical polymerization at the time of the bonding. In addition, the solvent is not a component that directly determines the adhesive property, but it is considered that an excessively large or excessively small content of the solvent in a coating formed of the dental adhesive composition applied in a cavity at the time of the bonding affects the polymerizability of chemical polymerization. In view of the foregoing, the inventors of the present invention judged that, in investigating the two-package dental adhesive composition according to this embodiment, it was also extremely important that evaluation be performed under a state in which the temperature environment in the mouth was reproduced as in "evaluation of floating amount of prosthesis" to be described later.

In addition, in actual dental treatment using a composite resin, the composite resin needs to be filled into a cavity in such a small space as the mouth. In addition, the shape of the cavity and the location where the cavity is formed in the mouth also vary from case to case. This means that treatment work in the mouth is liable to cause variations in work, such as the degree of force applied. It is considered that, as a result, the coating formed of the dental adhesive composition in an uncured state (adhesive layer in an uncured state) applied to the inner wall surface of the cavity is liable to be locally or entirely thinned more than necessary because the coating is crushed upon when the coating comes into contact with the composite resin filled into the mouth. Therefore, in the case where any of the related-art dental adhesive compositions is used, even when the thinned portion of the coating is cured as it is, the adhesive strength is reduced at this portion, with the result that adhesion failure between the tooth substance and the composite resin after curing is liable to be caused. Of course, the two-package dental adhesive composition according to this embodiment is excellent in adhesive property as compared to the related-art adhesive compositions, and hence does not cause such remarkable adhesion failure as described above. However, on the basis of the above-mentioned action mechanism, it is considered that the first composition tends to easily provide a more excellent adhesive property as compared to the second composition.

Further, in order to suppress the floating of the prosthesis in the bonding between the tooth substance and the prosthesis, it may be appropriate to use a prosthesis having a shape that more precisely corresponds to the shape of the cavity. However, even when such prosthesis is used, the floating occurs in some cases. The cause of the occurrence of such floating is considered to be as follows: the coating covering the inner wall surface of the cavity is significantly thickened at a portion in which a liquid accumulation is liable to occur, such as a corner portion in the cavity, instead of uniformly covering the entirety of the inner wall surface of the cavity. Therefore, in this case, even when the prosthesis having a precise shape is inserted and bonded into the cavity having the locally thick coating formed on the inner wall surface of the cavity, the prosthesis cannot be fitted in the cavity without excess or deficiency, and hence is bonded in a floating state.

However, those problems can be suppressed by using the first composition. That is, when the coating covering the inner wall surface of the cavity is formed by applying the first composition to the inner wall surface of the cavity, the low-boiling-point organic solvent, which relatively easily volatilizes, rapidly volatilizes first among the two kinds of organic solvents. Meanwhile, the high-boiling-point organic solvent volatilizes slowly and gradually. Accordingly, after a moderate increase in viscosity has been achieved by the rapid volatilization of the low-boiling-point organic solvent, a state in which the high-boiling-point organic solvent gradually volatilizes from the coating while the coating keeps a moderate viscosity is maintained over a long period of time.

In this case, even after the first composition has been applied to the inner wall surface of the cavity and the low-boiling-point organic solvent has rapidly volatilized from the coating formed on the inner wall surface, an appropriate amount of the high-boiling-point organic solvent remains in the coating over a long period of time. Accordingly, under such state, the coating can be easily deformed by air blowing while keeping moderate strength. Therefore, even when a significantly thick coating is formed at a portion in which a liquid accumulation is liable to occur, such as a corner portion in the cavity, the thickness of the coating covering the inner wall surface of the cavity can be easily uniformized by air blowing or the like for a while after application. Accordingly, when a prosthesis is fitted to a tooth using dental resin cement after the thickness of the coating covering the inner wall surface of the cavity has been uniformized by air blowing or the like, the prosthesis can be bonded without the occurrence of floating.

Meanwhile, when a composite resin is to be filled into a cavity, first, the first composition is applied to the inner wall surface of the cavity. After the application of the first composition, the low-boiling-point organic solvent rapidly volatilizes to provide a moderate viscosity, and hence the first composition can be easily uniformized into a coating having a moderate thickness by air blowing or the like. In addition, the high-boiling-point organic solvent remaining in the coating is also in a moderate amount, and hence can be sufficiently removed at the time of the air blowing. After the air blowing, curing with the gradually concentrated chemical polymerization initiators ((D) the borate compound and a chemical polymerization initiator other than (D) the borate compound, which is used as required) is accelerated from the time point of the volatilization of the low-boiling-point organic solvent, and hence a coating having moderate strength is formed. Therefore, the coating is less liable to be crushed at the time of the filling of the composite resin. In this case, a significant reduction in thickness of part or the entirety of an adhesive layer to be formed between the inner wall surface of the cavity and the cured composite resin can be suppressed, and as a result, a reduction in adhesive property can be suppressed. The same tendency is found in restoration using a prosthesis.

Here, in the first composition, the blending amount of the low-boiling-point organic solvent with respect to 100 parts by mass of the polymerization-reactive components is set to 200 parts by mass or more, and hence it becomes easier to secure a sufficient operation time. In addition, the blending amount is set to 400 parts by mass or less, and hence a reduction in adhesive property can be suppressed. The blending amount of the low-boiling-point organic solvent preferably falls within the range of from 250 parts by mass to 350 parts by mass.

In addition, the blending amount of the high-boiling-point organic solvent with respect to 100 parts by mass of the polymerization-reactive components is set to 25 parts by mass or more, and hence it becomes easier to secure a sufficient work time between the application of the first composition and the air blowing, and in the bonding of a prosthesis, the bonding of the prosthesis in a floating state can be more reliably suppressed. In addition, the blending amount is set to 120 parts by mass or less, and hence a reduction in adhesive property can be suppressed. The blending amount of the high-boiling-point organic solvent preferably falls within the range of from 50 parts by mass to 90 parts by mass.

Next, a first composition according to a more preferred embodiment is described. The blending amount of (E) the water in the first composition is not particularly limited, but (E) the water is blended within the range of preferably from 5 parts by mass to 50 parts by mass, more preferably from 20 parts by mass to 30 parts by mass with respect to 100 parts by mass of the polymerization-reactive components. When the blending amount is set to 5 parts by mass or more, it becomes easy to more improve the adhesive property for a tooth substance by decalcifying the surface of the tooth substance in the presence of (A) the acidic group-containing polymerizable monomer. In addition, when the blending amount is set to 50 parts by mass or less, a reduction in strength of the coating caused by an excess of the solvent components having relatively low volatilization rates (the high-boiling-point organic solvent and the water) in the coating at the time of the bonding can be suppressed, and hence it becomes easy to more improve the adhesive property.

In addition, a blending ratio between the high-boiling-point organic solvent and the low-boiling-point organic solvent is not particularly limited as long as the blending amount of the low-boiling-point organic solvent with respect to 100 parts by mass of the polymerization-reactive components is from 200 parts by mass to 400 parts by mass and the blending amount of the high-boiling-point organic solvent with respect to 100 parts by mass of the polymerization-reactive components is from 25 parts by mass to 120 parts by mass. However, the blending ratio is preferably from 2 to 12, more preferably from 3 to 7 in terms of mass ratio of the low-boiling-point organic solvent to the high-boiling-point organic solvent. When the mass ratio is set to 2 or more, it becomes easy to more improve the adhesive property, and when the mass ratio is set to 12 or less, in the bonding of a prosthesis, the bonding of the prosthesis in a floating state can be more reliably suppressed.

In the first composition, as the chemical polymerization initiator, (i) (D) the borate compound blended into the second agent may be used alone, or (ii) (D) the borate compound blended into the second agent may be used in combination with a chemical polymerization initiator other than (D) the borate compound, which is blended into at least one of the first agent or the second agent.

Here, the term "chemical polymerization initiator" as used herein also encompasses (H) the organic peroxide and (I) the decomposition accelerator, which are used for the purpose of further improving polymerization activity, as well as (D) the borate compound functioning as a polymerization accelerator. As such chemical polymerization initiator, from the viewpoint that high polymerization activity and high storage stability are obtained, (H) the organic peroxide and a vanadium compound serving as one kind of (I) the decomposition accelerator are suitably used in combination. Those chemical polymerization initiators may be appropriately blended into at least one of the first agent or the second agent, but from the viewpoint of storage stability, it is suitable that the vanadium compound be blended into the first agent and the organic peroxide be blended into the second agent. In addition, when the organic peroxide and the vanadium compound are used, from the viewpoint of more improving the storage stability, an arylborate compound is more preferably used as (D) the borate compound.

In addition, in the first composition, when a mixture obtained by mixing, at 23° C., only the whole amount of the polymerization-reactive components and the whole amount of the chemical polymerization initiator to be included in the composition is prepared, a curing time between commencing immediately after the mixing and ending on the completion of the curing of the mixture is preferably 60 seconds or less, more preferably 40 seconds or less, most preferably 30 seconds or less. For a general dental adhesive composition, from the viewpoint of securing a margin for the operation time, it is not preferred that the above-mentioned mixture be cured in 60 seconds or less at 23° C. That is, when the curing time is 60 seconds or less, the general dental adhesive composition causes a failure to perform a clinical operation or the thickening of a coating of the dental adhesive composition because the dental adhesive composition itself starts to cure during the work.

However, in the first composition, the solvent components can be added in a sufficient amount with respect to the polymerization-reactive components, and hence the polymerization-reactive components are diluted and an operation time with a sufficient margin is extremely easy to secure. Meanwhile, when the curing time of the mixture is set to 60 seconds or less, the mixture cures in a shorter period of time in a mouth at about 37° C. By virtue of this characteristic, it becomes easy to form a strong coating even when a dental composite resin or dental cement is pressed after the application of the first composition to the cavity. In addition, when a photocurable dental material, such as a dental composite resin, is subjected to photoirradiation, polymerization shrinkage of the photocurable dental material occurs, and hence detachment is liable to occur between a cured product of the photocurable dental material and the coating formed of the dental adhesive composition or a restoration target site. However, when the curing time is set to 60 seconds or less, the coating formed of the first composition can be sufficiently polymerized to firmly bond the cured product and the restoration target site to each other within a period of time between the filling of the restoration target site with the photocurable dental material and the photoirradiation. Accordingly, the detachment as described above can be suppressed.

Further, the first composition having a curing time of 60 seconds or less has high polymerization activity, and hence can obtain excellent curability through only chemical polymerization. Accordingly, there is no need to add a photopolymerization initiator to the first composition. Consequently, a step of subjecting the first composition to photoirradiation can be omitted, and hence the work time can be shortened to reduce burdens on a dentist and a patient.

Meanwhile, when the curing time is excessively short, there is a risk in that floating of the dental cement may occur. Therefore, the curing time is preferably at least 1 second or more, more preferably 3 seconds or more. The curing time may be controlled to a desired period of time by appropriately selecting the composition and blending amount of the chemical polymerization initiator.

Dental Treatment Method

A dental treatment method using the two-package dental adhesive composition according to this embodiment includes at least a composition-applying step of applying the two-package dental adhesive composition according to this embodiment to any of various adherends, such as a tooth substance and a noble metal. The composition-applying step is generally carried out by mixing the first agent and the second agent with each other to prepare a mixed composition, and then applying the mixed composition to the surface of an adherend, such as a tooth substance. However, the composition-applying step may be carried out by simultaneously applying or separately and sequentially applying the first agent and the second agent to the surface of the adherend. In this case, the first agent and the second agent are mixed with each other on the surface of the adherend.

In addition, the dental treatment method using the two-package dental adhesive composition according to this embodiment is not particularly limited as long as the two-package dental adhesive composition according to this embodiment is used for bonding between two adherends, but typical examples thereof include dental treatment methods to be described below.

That is, a dental treatment method according to a first embodiment of the present invention includes at least: a first composition-applying step of applying the two-package dental adhesive composition according to this embodiment to a surface of a tooth (tooth substance); a second composition-applying step of applying a photopolymerizable dental composition, which includes a polymerizable monomer, a filler, and a photopolymerization initiator, to the surface of the tooth having applied thereto the two-package dental adhesive composition according to this embodiment; and a photoirradiation step of subjecting the surface of the tooth having applied thereto the two-package dental adhesive composition according to this embodiment and the photopolymerizable dental composition to photoirradiation. Herein, the photopolymerizable dental composition is what is generally called a composite resin.

As the polymerizable monomer, the filler, and the photopolymerization initiator to be used for the photopolymerizable dental composition, known ones, including those to be used for the two-package dental adhesive composition according to this embodiment, may be utilized in appropriate combination.

In addition, a dental treatment method according to a second embodiment of the present invention includes at least: a first composition-applying step of applying the two-package dental adhesive composition according to this embodiment to a surface of an adherend selected from the group consisting of a tooth substance, a base metal, a noble metal, a metal oxide, a silica-based oxide, a composite resin material, and a composite material obtained by combining two or more kinds thereof; and a second composition-applying step of applying a chemically polymerizable dental composition, which includes a polymerizable monomer, a filler, and a chemical polymerization initiator, to the surface of the adherend having applied thereto the two-package dental adhesive composition according to this embodiment. Herein, the chemically polymerizable dental composition is what is generally called a resin core or resin cement.

As the polymerizable monomer to be used for the chemically polymerizable dental composition, known ones, including the polymerizable monomers and fillers that may be used for the two-package dental adhesive composition according to this embodiment, may be appropriately utilized.

In addition, as the chemical polymerization initiator, a known chemical polymerization initiator may be used, and a chemical polymerization initiator containing an organic peroxide and an amine compound is preferably used.

Here, examples of the organic peroxide include: hydroperoxides, such as t-butyl hydroperoxide and cumene hydroperoxide; dialkyl peroxides, such as di-t-butyl peroxide and dicumyl peroxide; and diacyl peroxides, such as acetyl peroxide, lauroyl peroxide, and benzoyl peroxide. Those organic peroxides may be used alone or as a mixture thereof.

Of those organic peroxides, from the viewpoints of, for example, the polymerization activity and storage stability of a combination with a tertiary amine, a diacyl peroxide is preferred, and benzoyl peroxide is most suitably used.

In addition, a tertiary amine compound may be used as the amine compound. In general, tertiary amine compounds are broadly classified into an aromatic tertiary amine in which an aromatic group is bonded to a nitrogen atom, and an aliphatic tertiary amine in which only aliphatic groups are bonded to a nitrogen atom.

Here, examples of the aromatic tertiary amine may include: toluidine-based aromatic tertiary amines, such as N,N-dimethyl-p-toluidine, N,N-diethyl-p-toluidine, N,N-dimethyl-m-toluidine, N,N-dihydroxyethyl-p-toluidine, and N,N-dimethyl-3,5-xylidine; aniline-based aromatic tertiary amines, such as N,N-dimethylaniline, N,N-diethylaniline, N,N-di-n-butylaniline, N,N-dibenzylaniline, p-bromo-N,N-dimethylaniline, m-chloro-N,N-dimethylaniline, and N,N-dihydroxyethylaniline; aromatic tertiary amines in each of which a carbonyl group is bonded to an aromatic ring, such as p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, and N,N-dimethylanthranilic acid methyl ester; and p-dimethylaminophenethyl alcohol, p-dimethylaminostilbene, 4-dimethylaminopyridine, N,N-dimethyl-α-naphthylamine, and N,N-dimethyl-α-naphthylamine.

In addition, examples of the aliphatic tertiary amine include tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol.

The amine compounds may be used alone or as a mixture thereof.

In the polymerization and curing of the chemically polymerizable dental composition using the chemical polymerization initiator containing the organic peroxide and the amine compound, when an acidic group-containing polymerizable monomer is present in the system, in general, an acidic group of the acidic group-containing polymerizable monomer neutralizes the amine compound. In this case, the polymerization activity of the chemical polymerization initiator is significantly reduced, resulting in a curing defect.

However, when the chemically polymerizable dental composition using the chemical polymerization initiator containing the organic peroxide and the amine compound is applied to the surface of the adherend having applied thereto the two-package dental adhesive composition according to this embodiment, the acidic group-containing polymerizable monomer contained in the first agent of the two-package dental adhesive composition according to this embodiment does not cause such curing defect as described above. This is because the borate compound contained in the second agent of the two-package dental adhesive composition reacts with the acidic group-containing polymerizable monomer to generate a radical, with the result that the polymerization activity of the chemical polymerization initiator contained in the chemically polymerizable dental composition is not inhibited.

The chemically polymerizable dental composition may be a so-called dual-cure chemically polymerizable dental composition, which further includes a photopolymerization initiator and can be cured by each of photopolymerization and chemical polymerization.

In addition, the mode of treatment of a tooth in the case of using the first composition as the two-package dental adhesive composition according to this embodiment is not particularly limited, but restoration further using a composite resin in combination therewith, or restoration further using a prosthesis in combination therewith is suitable.

For example, in a process of restoring a tooth further using a composite resin, at least the following steps may be carried out in the stated order: (i) a step of applying the first composition to an inner wall surface of a cavity; (ii) a step of subjecting a coating containing the first composition formed on the inner wall surface of the cavity to air blowing, to thereby remove excess organic solvent components and water from the coating to uniformize the coating; (iii) a step of filling the composite resin into the cavity having the coating formed on the inner wall surface thereof; and (iv) a step of curing the composite resin filled into the cavity by photoirradiation.

In (i) the step of applying the first composition to an inner wall surface of a cavity, in ordinary cases, a) a mixed liquid obtained by mixing the first agent and the second agent with each other is prepared in advance, and then the mixed liquid is applied to the inner wall surface of the cavity. However, b) the first agent and the second agent may be mixed with each other on the inner wall surface of the cavity by applying any one of the first agent and the second agent to the inner wall surface of the cavity, and then further applying the other, or c) the first agent and the second agent may be simultaneously applied to the inner wall surface of the cavity, and simultaneously with this, be mixed with each other.

In addition, in a process of restoring a tooth further using a prosthesis, at least the following steps may be carried out in the stated order: (i) a step of applying the first composition to an inner wall surface of a cavity (and/or a surface of the prosthesis); (ii) a step of subjecting a coating containing the first composition formed on the inner wall surface of the cavity (and/or the surface of the prosthesis) to air blowing, to thereby remove excess organic solvent components and water from the coating to uniformize the coating; (iii) a step of applying dental resin cement to the inner wall surface of the cavity (and/or the surface of the prosthesis); and (iv) a step of inserting the prosthesis into the cavity and fitting the prosthesis to the tooth.

In (i) the step of applying the first composition to an inner wall surface of a cavity (and/or a surface of the prosthesis), in ordinary cases, a) a mixed liquid obtained by mixing the first agent and the second agent is prepared in advance, and then the mixed liquid is applied to the inner wall surface of the cavity (and/or the surface of the prosthesis). However, b) the first agent and the second agent may be mixed with each other on the inner wall surface of the cavity (and/or the surface of the prosthesis) by applying any one of the first agent and the second agent to the inner wall surface of the cavity (and/or the surface of the prosthesis), and then further applying the other, or c) the first agent and the second agent may be simultaneously applied to the inner wall surface of the cavity (and/or the surface of the prosthesis), and simultaneously with this, be mixed with each other.

EXAMPLES

Now, the present invention is described by way of Examples, but the present invention is not limited only to the following Examples.

1. Abbreviations of Substances

Abbreviations of substances used in dental adhesive compositions of Examples and Comparative Examples are described below.

(A) Acidic Group-containing Polymerizable Monomer
MDP: 10-Methacryloxydecyl dihydrogen phosphate
MHP: 6-Methacryloxyhexyl dihydrogen phosphate
PM1: Mono(2-methacryloxyethyl)acid phosphate
PM2: Bis(2-methacryloxyethyl)acid phosphate
PMB2: Bis(2-methacryloxybutyl)acid phosphate (B) Sulfur Atom-containing Polymerizable Monomer
MTU-6: 6-Methacryloyloxyhexyl 2-thiouracil-5-carboxylate
MMT-11: 2-(11-Methacryloyloxyundecylthio)-5-mercapto-1,3,4-thiadiazole (C) Silane Coupling Agent
MPS: γ-Methacryloxypropyltrimethoxysilane
MPTES: γ-Methacryloxypropyltriethoxysilane (D) Borate Compound
PhB-TEOA: Triethanolamine salt of tetraphenylboron
PhB—Na: Sodium salt of tetraphenylboron (F) Organic Solvent
High-Boiling-Point Organic Solvent
IPA: Isopropyl alcohol (G) Other Polymerizable Monomer
BisGMA: 2,2'-Bis[4-(2-hydroxy-3-methacryloxypropoxy)phenyl]propane
3G: Triethylene glycol dimethacrylate
HEMA: 2-Hydroxyethyl methacrylate
Other Component
BMOV: Oxovanadium(IV) bis(maltolate)
PEROCTA H: 1,1,3,3-Tetramethylbutyl hydroperoxide
CQ: Camphorquinone
DMBE: Ethyl 4-dimethylaminobenzoate
BPO: Benzoyl peroxide
DEPT: N,N-Dimethyl-p-toluidine
PTSNa: Sodium p-toluenesulfinate
Cu—AcAc: Copper acetylacetonate
MBI: 2-Mercaptobenzimidazole 2. Preparation of Dental Adhesive Compositions The respective components were mixed as shown in Table 1 to Table 4 to prepare two-package dental adhesive compositions each formed of a first agent and a second agent. However, the dental adhesive composition shown in Comparative Example 11 was a one-package dental adhesive composition formed only of a first agent.

3. Evaluation of Adhesive Strength between Tooth Substance and Composite Resin

Adherends obtained by polishing a bovine front tooth extracted within 24 hours after killing with waterproof abrasive paper P600 under a flow of water to carve out an enamel plane and a dentin plane, respectively, so as to be parallel to a labial surface and flat were prepared.

Next, a double-sided tape perforated with a hole having a diameter of 3 mm was attached to the polished surface of each of those two kinds of adherends. Subsequently, the dental adhesive composition of each of Examples and Comparative Examples shown in Table 1 to Table 4 was applied to a bonding surface, which was exposed from the hole of the double-sided tape, in the polished surface, and was dried by air blowing for 5 seconds.

The dental adhesive composition was applied to the bonding surface after the first agent and the second agent had been turned to a mixed liquid on a mixing dish. A mixing ratio between the first agent and the second agent was set so that the blending ratio of each component shown in Table 1 to Table 4 was maintained as it was. For example, in the case of Example 1, 250 parts by mass of the second agent was mixed with 250 parts by mass of the first agent. In addition, in the case of the one-package dental adhesive composition formed only of the first agent, only the first agent was applied to the bonding surface.

In addition, as the dental adhesive composition to be applied to the bonding surface, the following two kinds were used: a dental adhesive composition immediately after its preparation; and a dental adhesive composition that, after its preparation, had been sealed in a container and further stored in a thermostatic chamber at 50° C. for 8 weeks. The first agent of each of the dental adhesive compositions of Comparative Examples 8 and 11 gelled in about 1 hour after its preparation. Therefore, in the case of applying the dental adhesive composition immediately after its preparation to the bonding surface, the components for the first agent except for the borate compound were mixed, and then the borate compound was added to prepare the first agent immediately before its use. Then, in Comparative Example 8, immediately after the preparation of the first agent, the first agent and the second agent were mixed with each other and applied to the bonding surface, and in Comparative Example 11, immediately after the preparation of the first agent, the first agent was applied to the bonding surface.

A paraffin wax having a hole with a diameter of 8 mm and having a thickness of 0.5 mm was attached to the bonding surface having applied thereto the dental adhesive composition so that the hole of the paraffin wax and the hole of the double-sided tape were concentric with each other, to thereby produce a simulated cavity. A dental composite resin (Estelite Σ Quick, manufactured by Tokuyama Dental Corporation) was filled into the simulated cavity and lightly pressed with a polyester film, and then photocured by photoirradiation for 10 seconds using a visible light irradiator (TOKUSO POWER LITE, manufactured by Tokuyama Corporation). After that, a round bar made of SUS304

(diameter: 8 mm, height: 18 mm) that had been polished in advance was bonded using resin cement (BISTITE II, manufactured by Tokuyama Dental Corporation). Finally, the resultant was immersed in water at 37° C. for 24 hours to provide a sample for adhesive strength measurement. The composite resin used (Estelite Σ Quick) is a photopolymerizable composition containing camphorquinone and an amine compound.

For each of such samples, tensile adhesive strength was measured using Autograph manufactured by Shimadzu Corporation (cross-head speed: 2 mm/min). For each of Examples and Comparative Examples, the measured values of four samples were averaged to give a measurement result. In addition, the measurement was carried out within about 1 day after the lifting of the sample for adhesive strength measurement out of the water.

The measurement results of the adhesive strengths of samples each obtained by applying a dental adhesive composition immediately after its preparation to the bonding surface (initial adhesive strength) are shown in Table 5 and Table 6, and the measurement results of the adhesive strengths of samples each obtained by applying a dental adhesive composition that, after its preparation, had been further stored in a thermostatic chamber at 50° C. for 8 weeks to the bonding surface (adhesive strength after long-term storage) are shown in Table 7 and Table 8. In addition, immersion treatment involving alternately immersing the samples, each obtained by applying a dental adhesive composition immediately after its preparation to the bonding surface, in a water bath having a water temperature of 5° C. and a water bath having a water temperature of 55° C. for 30 seconds each, which was defined as one set, had been further carried out repeatedly 3,000 times. The measurement results of the adhesive strengths of resultant samples each obtained by the 3,000 times repeated immersion treatments (adhesive strength after endurance test) are shown in Table 9.

When any one of the first agent or the second agent gelled in appearance evaluation after long-term storage to be described later, it became difficult to apply the dental adhesive composition to the bonding surface, and hence the evaluation of adhesive strength after long-term storage was omitted.

4. Evaluation of Adhesive Strength between Various Adherends and Resin Cement

The following seven kinds of adherends were prepared.
(1) An adherend obtained by polishing a bovine front tooth extracted within 24 hours after killing with waterproof abrasive paper P600 under a flow of water to carve out an enamel plane so as to be parallel to a labial surface and flat.
(2) An adherend obtained by polishing a bovine front tooth extracted within 24 hours after killing with waterproof abrasive paper P600 under a flow of water to carve out a dentin plane so as to be parallel to a labial surface and flat.
(3) An adherend formed of a noble metal alloy obtained by polishing a dental gold-silver-palladium alloy "GOLD-PALLADIUM 12" (manufactured by Towa Giken Co., Ltd., 10 mm long×10 mm wide×3 mm thick) with #1500 waterproof abrasive paper and then subjecting the resultant to sandblasting treatment.
(4) An adherend formed of a base metal alloy obtained by polishing a dental cobalt-chromium alloy "WORCHROME" (manufactured by Towa Giken Co., Ltd., 10 mm long×10 mm wide×3 mm thick) with #1500 waterproof abrasive paper and then subjecting the resultant to sandblasting treatment.
(5) An adherend formed of a silica-based oxide (porcelain) obtained by polishing a silica-based oxide "Gcera Cosmotec II" (manufactured by GC Corporation, 10 mm long×10 mm wide×3 mm thick) with #1500 waterproof abrasive paper and then subjecting the resultant to sandblasting.
(6) An adherend formed of a composite resin material obtained by polishing a composite resin material "ESTELITE BLOCK" (manufactured by Tokuyama Dental Corporation, 10 mm long×10 mm wide×3 mm thick) with #1500 waterproof abrasive paper and then subjecting the resultant to sandblasting. "ESTELITE BLOCK" is a composite resin material containing silica particles in a resin matrix.
(7) An adherend formed of a metal oxide (zirconia ceramics) obtained by polishing zirconia ceramics "TZ-3Y-E sintered body" (manufactured by Tosoh Corporation, 10 mm long×10 mm wide×3 mm thick) with #1500 waterproof abrasive paper and then subjecting the resultant to sandblasting.

Next, a double-sided tape perforated with a hole having a diameter of 3 mm was attached to the polished surface of each of those seven kinds of adherends. Subsequently, the dental adhesive composition of each of Examples and Comparative Examples shown in Table 1 to Table 4 was applied to a bonding surface, which was exposed from the hole of the double-sided tape, in the polished surface, and was dried by air blowing for 5 seconds.

The dental adhesive composition was applied to the bonding surface after the first agent and the second agent had been turned to a mixed liquid on a mixing dish. A mixing ratio between the first agent and the second agent was set so that the blending ratio of each component shown in Table 1 to Table 4 was maintained as it was. For example, in the case of Example 2, 250 parts by mass of the second agent was mixed with 250.1 parts by mass of the first agent. In addition, in the case of the one-package dental adhesive composition formed only of the first agent, only the first agent was applied to the bonding surface.

In addition, as the dental adhesive composition to be applied to the bonding surface, the following two kinds were used: a dental adhesive composition immediately after its preparation; and a dental adhesive composition that, after its preparation, had been sealed in a container and further stored in a thermostatic chamber at 50° C. for 8 weeks. The first agent of each of the dental adhesive compositions of Comparative Examples 8 and 11 gelled in about 1 hour after its preparation. Therefore, in the case of applying the dental adhesive composition immediately after its preparation to the bonding surface, the components for the first agent except for the borate compound were mixed, and then the borate compound was added to prepare the first agent immediately before its use. Then, in Comparative Example 8, immediately after the preparation of the first agent, the first agent and the second agent were applied to the bonding surface, and in Comparative Example 11, immediately after the preparation of the first agent, the first agent was applied to the bonding surface.

Subsequently, a round bar made of SUS304 (diameter: 8 mm, height: 18 mm), which had been polished in advance and had applied thereto the dental adhesive composition, was further bonded to the bonding surface having applied thereto the dental adhesive composition using dental adhesive resin cement (ESTECEM, manufactured by Tokuyama Dental Corporation). Excess resin cement protruding from the bonding surface at the time of the bonding was removed using a needle and the like. After that, the resultant was left to stand in a thermostatic chamber kept at a temperature of 37° C. and a humidity of 100% for about 1 hour to allow the dental adhesive resin cement to be chemically polymerized. Finally, the resultant was immersed in water at 37° C. for 24 hours to provide a sample for adhesive strength measurement. The dental adhesive resin cement used contains a photopolymerization initiator and a benzoyl peroxide-amine compound-based chemical polymerization initiator, and its polymerization and curing can be performed by each of photopolymerization and chemical polymerization. In this bonding test, the resin cement was cured utilizing only chemical polymerization.

For each of such samples, tensile adhesive strength was measured using Autograph manufactured by Shimadzu Corporation (cross-head speed: 2 mm/min). For each of Examples and Comparative Examples, the measured values of four samples were averaged to give a measurement result. In addition, the measurement was carried out within about 1 day after the lifting of the sample for adhesive strength measurement out of the water.

The measurement results of the adhesive strengths of samples each obtained by applying a dental adhesive composition immediately after its preparation to the bonding surface (initial adhesive strength) are shown in Table 5 and Table 6, and the measurement results of the adhesive strengths of samples each obtained by applying a dental adhesive composition that, after its preparation, had been further stored in a thermostatic chamber at 50° C. for 8 weeks to the bonding surface (adhesive strength after long-term storage) are shown in Table 7 and Table 8. In addition, immersion treatment involving alternately immersing the samples, each obtained by applying a dental adhesive composition immediately after its preparation to the bonding surface, in a water bath having a water temperature of 5° C. and a water bath having a water temperature of 55° C. for 30 seconds each, which was defined as one set, had been further carried out repeatedly 3,000 times. The measurement results of the adhesive strengths of resultant samples each obtained by the 3,000 times repeated immersion treatments (adhesive strength after endurance test) are shown in Table 9.

When any one of the first agent or the second agent gelled in appearance evaluation after long-term storage to be described later, it became difficult to apply the dental adhesive composition to the bonding surface, and hence the evaluation of adhesive strength after long-term storage was omitted.

5. Appearance Evaluation after Long-term Storage

The dental adhesive composition of each of Examples and Comparative Examples shown in Table 1 to Table 4 was, after its preparation, sealed in a container and further stored in a thermostatic chamber at 50° C. for 8 weeks. Subsequently, after having been removed from the thermostatic chamber, the container in which the first agent was sealed and the container in which the second agent was sealed were each visually observed for its appearance, and evaluations were performed for the presence or absence of changes in the first agent and the second agent before and after the storage, and denaturation, such as gelation. The results are shown in Table 7 and Table 8.

6. Measurement of Operation Time

An operation time was measured for each of the dental adhesive compositions of Examples 2, 6, 7, 8, and 9, and Comparative Examples 14, 15, 16, and 17. The measurement of the operation time was carried out by the following procedure. First, under a normal-temperature and normal-humidity environment (temperature: 23° C., humidity: 50%), 0.04 ml of the dental adhesive composition of each of Examples and Comparative Examples was collected in a mixing dish. In the case of a two-package dental adhesive composition, the first agent and the second agent were mixed with each other in the mixing dish simultaneously with being collected. Subsequently, after the lapse of a predetermined period of time with the time point of the collection being defined as 0 seconds, the dental adhesive composition collected in the mixing dish was applied to the surface of an adherend sample (enamel plane carved out so as to be parallel to a labial surface and flat by polishing a bovine front tooth extracted within 24 hours after killing with waterproof abrasive paper P600 under a flow of water) using a mini brush. In this application test, application with a mini brush was performed once every time the dental adhesive composition was collected in a mixing dish, which was defined as one set, and every time the time it took from the collection to the application was changed, the dental adhesive composition was freshly collected in a mixing dish and its application with a mini brush was carried out. In addition, in the application, whether applicability was satisfactory was judged on the basis of whether the dental adhesive composition was able to be smoothly and sufficiently spread on the surface of the adherend sample with the mini brush, and the maximum time at which satisfactory applicability was shown was defined as the operation time. The results are shown in Table 10. A standard for an appropriate operation time is 60 seconds or more.

7. Evaluation of Floating Amount of Prosthesis

The floating amount of a prosthesis was evaluated for each of the dental adhesive compositions of Examples 2, 6, 7, 8, and 9, and Comparative Examples 15 and 17. The evaluation of the floating amount of the prosthesis was carried out by the following procedure. First, with the use of a model tooth made of a resin having formed therein a class 1 cavity having a remarkable corner portion in the cavity, a composite resin (Estelite Flow Quick, manufactured by Tokuyama Dental Corporation) was filled into the cavity, and further, the composite resin was cured by photoirradiation. Next, the surface of the model tooth on the side where the opening of the cavity was formed was polished together with the composite resin cured in the cavity (prosthesis formed of a composite resin material), and in this manner, polishing was performed so that the upper surface of the prosthesis in the cavity and the surface of the model tooth around the opening of the cavity became completely flush with each other (step: 0 μm). Then, after the polishing, the prosthesis was removed from the cavity.

Next, to each of the inner wall surface of the cavity and the surface of the prosthesis (surface to be brought into contact with the inner wall surface of the cavity), the dental adhesive composition of each of Examples and Comparative Examples was applied, and dental resin cement (ESTECEM, manufactured by Tokuyama Dental Corporation) was further applied thereon. Subsequently, the prosthesis was inserted into the cavity, and the prosthesis was fitted to the model tooth. In the case of a two-package dental adhesive composition, the first agent and the second agent were turned to a mixed liquid on a mixing dish, and the mixed liquid was applied to a bonding surface. After that, excess dental resin cement protruding from the bonding interface between the cavity and the prosthesis was removed, and the dental resin cement was cured by photoirradiation. Thus, a sample for the evaluation of the floating amount of the prosthesis was obtained. During the application work of the dental adhesive composition and the dental resin cement, the temperature of the model tooth was set to a temperature (37° C.) equivalent to that in the mouth. In addition, after the application of the dental adhesive composition into the cavity, air blowing was carried out for about 5 seconds in order to suppress the formation of a thick coating at a corner portion in the cavity.

For the resultant sample, a step between the surface of the model tooth around the opening of the cavity and the upper surface of the prosthesis was measured using a laser microscope at each of four sites every about 90 degrees along the circumferential direction of the upper surface of the prosthesis, and the average value of the steps at the four sites was defined as the floating amount of the prosthesis. The results are shown in Table 10. In actual clinical practice, a prosthesis is produced in a size having a space of 50 µm or more with respect to a cavity, and hence a case in which the floating amount of the prosthesis in this test is 50 µm or less is judged satisfactory.

8. Measurement of Curing Time

A curing time was evaluated for each of the dental adhesive compositions of Examples 2, 6, 7, 8, and 9, and Comparative Examples 14, 15, 16, and 17. The measurement of the curing time was carried out by mixing the whole amount of the polymerization-reactive components and the whole amount of the chemical polymerization initiators out of the respective constituent components of the dental adhesive composition of each of Examples and Comparative Examples. Here, when the dental adhesive composition used in the evaluation further included a chemical polymerization initiator other than (D) the borate compound, mutually reactive components among the plurality of kinds of chemical polymerization initiators were separated from each other to prepare a first liquid in which one of the components was mixed and dissolved in part of the whole amount of the polymerization-reactive components, and a second liquid in which the other component was mixed and dissolved in the remainder of the whole amount of the polymerization-reactive components. After that, a mixture obtained by mixing the first liquid and the second liquid with each other at 23° C. was prepared, and immediately after the mixing, was put into a sample dish to which a thermocouple was attached. Then, a curing time between commencing immediately after the mixing and ending on the completion of the curing of the mixture was measured. The completion of the curing was defined as a time point at which a temperature detected with the thermocouple showed a maximum value. The results are shown in Table 10.

9. Evaluation of Adhesive Layer Thickness in Restoration using Composite Resin

An adhesive layer thickness in restoration using a composite resin was evaluated for each of the dental adhesive compositions of Examples 2, 6, 7, 8, and 9, and Comparative Examples 14, 15, 16, and 17. The adhesive layer thickness in restoration using a composite resin was evaluated by the following procedure. First, an adherend obtained by polishing a bovine front tooth extracted within 24 hours after killing with waterproof abrasive paper P600 under a flow of water to carve out a dentin plane so as to be parallel to a labial surface and flat was prepared.

Next, the dental adhesive composition of each of Examples and Comparative Examples was applied to the polished surface of the adherend, and air blowing was carried out for about 5 seconds. The application was performed as follows: the first agent and the second agent were turned to a mixed liquid on a mixing dish, and the mixed liquid was applied to the adherend. Subsequently, a composite resin (Estelite Σ Quick, manufactured by Tokuyama Dental Corporation) was pressed against the surface having applied thereto the dental adhesive composition, and then the composite resin was cured by photoirradiation to provide a sample for adhesive layer thickness evaluation. The resultant sample was cut along a direction orthogonal to the polished surface of the adherend, and the thickness of an adhesive layer (cured product of the dental adhesive composition) exposed on the cut surface was measured with a laser microscope. The results are shown in Table 10. From the viewpoint of the suppression of adhesion failure or the like, it is judged that an appropriate range of the thickness of the adhesive layer is from 5 µm to 25 µm.

TABLE 1

| | | Example 1 | Example 2 | Example 3 | Example 4 | Example 5 |
|---|---|---|---|---|---|---|
| First agent | (A) Acidic group-containing polymerizable monomer | MDP (90) | MDP (15) | MDP (15) | MDP (15) | MDP (15) |
| | (B) Sulfur atom-containing polymerizable monomer | MTU-6 (10) | MTU-6 (0.1) | MTU-6 (0.1) | MTU-6 (0.1) | MTU-6 (0.1) |
| | Organic solvent | Acetone (150) | Acetone (150) | Acetone (150) | Acetone (150) | Acetone (150) |
| | Other polymerizable monomer | — | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
| | Other component | — | BMOV (0.1) | BMOV (0.1) | BMOV (0.1) | BMOV (0.1) |
| Second agent | (C) Silane coupling agent | MPS (8) | MPTES (8) | MPS (8) | MPS (8) | MPTES (8) |
| | (D) Borate compound | PhB-TEOA (4) | PhB—Na (4) | PhB—Na (4) | PhB-TEOA (4) | PhB-TEOA (4) |
| | (E) Water | Water (25) | Water (25) | Water (25) | Water (25) | Water (25) |
| | Organic solvent | Acetone (153) IPA (60) | Acetone (150) IPA (60) | Acetone (150) IPA (60) | Acetone (150) IPA (60) | Acetone (150) IPA (60) |
| | Other component | — | PEROCTA H (3) | PEROCTA H (3) | PEROCTA H (3) | PEROCTA H (3) |

| | | Example 6 | Example 7 | Example 8 | Example 9 |
|---|---|---|---|---|---|
| First agent | (A) Acidic group-containing polymerizable monomer | MDP (15) | MDP (15) | MDP (15) | MDP (15) |
| | (B) Sulfur atom-containing polymerizable monomer | MTU-6 (0.1) | MTU-6 (0.1) | MTU-6 (0.1) | MTU-6 (0.1) |
| | Organic solvent | Acetone (200) | Acetone (110) | Acetone (180) | Acetone (135) |
| | Other polymerizable monomer | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
| | Other component | BMOV (0.1) | BMOV (0.1) | BMOV (0.1) | BMOV (0.1) |
| Second agent | (C) Silane coupling agent | MPTES (8) | MPTES (8) | MPTES (8) | MPTES (8) |
| | (D) Borate compound | PhB—Na (4) | PhB—Na (4) | PhB—Na (4) | PhB—Na (4) |
| | (E) Water | Water (25) | Water (25) | Water (25) | Water (25) |

TABLE 1-continued

|  |  |  |  |  |  |
|---|---|---|---|---|---|
|  | Organic solvent | Acetone (200) IPA (60) | Acetone (110) IPA (60) | Acetone (120) IPA (120) | Acetone (165) IPA (30) |
|  | Other component | PEROCTA H (3) | PEROCTA H (3) | PEROCTA H (3) | PEROCTA H (3) |

|  |  |  | Example 10 | Example 11 | Example 12 | Example 13 |
|---|---|---|---|---|---|---|
| First agent | (A) Acidic group-containing polymerizable monomer | | MDP (15) | MDP (15) | MDP (15) | MDP (15) |
|  | (B) Sulfur atom-containing polymerizable monomer | | MTU-6 (0.1) | MTU-6 (0.1) | MTU-6 (0.1) | MTU-6 (0.1) |
|  | Organic solvent | | Acetone (150) | Ethanol (150) | Acetone (70) | Acetone (100) |
|  | Other polymerizable monomer | | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
|  | Other component | | BMOV (0.1) | BMOV (0.1) | BMOV (0.1) | BMOV (0.1) |
| Second agent | (C) Silane coupling agent | | MPTES (8) | MPTES (8) | MPTES (8) | MPTES (8) |
|  | (D) Borate compound | | PhB—Na (4) | PhB—Na (4) | PhB—Na (4) | PhB—Na (4) |
|  | (E) Water | | Water (25) | Water (25) | Water (25) | Water (25) |
|  | Organic solvent | | Acetone (210) | Ethanol (210) | Acetone (70) IPA (60) | Acetone (150) IPA (10) |
|  | Other component | | PEROCTA H (3) | PEROCTA H (3) | PEROCTA H (3) | PEROCTA H (3) |

TABLE 2

|  |  | Example 14 | Example 15 | Example 16 | Example 17 |
|---|---|---|---|---|---|
| First agent | (A) Acidic group-containing polymerizable monomer | MDP (3) | MDP (6) | MDP (28) | MDP (35) |
|  | (B) Sulfur atom-containing polymerizable monomer | MTU-6 (0.1) | MTU-6 (0.1) | MTU-6 (0.1) | MTU-6 (0.1) |
|  | Organic solvent | Acetone (150) | Acetone (150) | Acetone (150) | Acetone (150) |
|  | Other polymerizable monomer | BisGMA (41), 3G (27), HEMA (28.9) | BisGMA (40), 3G (26), HEMA (27.9) | BisGMA (31), 3G (20), HEMA (20.9) | BisGMA (28), 3G (18), HEMA (18.9) |
|  | Other component | BMOV (0.1) | BMOV (0.1) | BMOV (0.1) | BMOV (0.1) |
| Second agent | (C) Silane coupling agent | MPTES (8) | MPTES (8) | MPTES (8) | MPTES (8) |
|  | (D) Borate compound | PhB—Na (4) | PhB—Na (4) | PhB—Na (4) | PhB—Na (4) |
|  | (E) Water | Water (25) | Water (25) | Water (25) | Water (25) |
|  | Organic solvent | Acetone (150) IPA (60) | Acetone (150) IPA (60) | Acetone (150) IPA (60) | Acetone (150) IPA (60) |
|  | Other component | PEROCTA H (3) | PEROCTA H (3) | PEROCTA H (3) | PEROCTA H (3) |

|  |  | Example 18 | Example 19 | Example 20 | Example 21 | Example 22 |
|---|---|---|---|---|---|---|
| First agent | (A) Acidic group-containing polymerizable monomer | MDP (15), PM2 (3) | MDP (15), PM1 (3) | MDP (15), PMB2 (3) | MDP (15), PM2 (0.1) | MDP (15), PM2 (1) |
|  | (B) Sulfur atom-containing polymerizable monomer | MTU-6 (0.1) | MTU-6 (0.1) | MTU-6 (0.1) | MTU-6 (0.1) | MTU-6 (0.1) |
|  | Organic solvent | Acetone (150) | Acetone (150) | Acetone (150) | Acetone (150) | Acetone (150) |
|  | Other polymerizable monomer | BisGMA (35), 3G (23), HEMA (23.9) | BisGMA (35), 3G (23), HEMA (23.9) | BisGMA (35), 3G (23), HEMA (23.9) | BisGMA (36), 3G (24), HEMA (24.8) | BisGMA (35), 3G (24), HEMA (24.9) |
|  | Other component | BMOV (0.1) | BMOV (0.1) | BMOV (0.1) | BMOV (0.1) | BMOV (0.1) |
| Second agent | (C) Silane coupling agent | MPTES (8) | MPTES (8) | MPTES (8) | MPTES (8) | MPTES (8) |
|  | (D) Borate compound | PhB—Na (4) | PhB—Na (4) | PhB—Na (4) | PhB—Na (4) | PhB—Na (4) |
|  | (E) Water | Water (25) | Water (25) | Water (25) | Water (25) | Water (25) |
|  | Organic solvent | Acetone (150) IPA (60) | Acetone (150) IPA (60) | Acetone (150) IPA (60) | Acetone (150) IPA (60) | Acetone (150) IPA (60) |
|  | Other component | PEROCTA H (3) | PEROCTA H (3) | PEROCTA H (3) | PEROCTA H (3) | PEROCTA H (3) |

|  |  | Example 23 | Example 24 | Example 25 | Example 26 |
|---|---|---|---|---|---|
| First agent | (A) Acidic group-containing polymerizable monomer | MDP (15), PM2 (5) | MDP (15), PM2 (15) | PM2 (15) | MHP (15) |
|  | (B) Sulfur atom-containing polymerizable monomer | MTU-6 (0.1) | MTU-6 (0.1) | MTU-6 (0.1) | MTU-6 (0.1) |
|  | Organic solvent | Acetone (150) | Acetone (150) | Acetone (150) | Acetone (150) |
|  | Other polymerizable | BisGMA (34), | BisGMA (30), | BisGMA (36), | BisGMA (36), |

TABLE 2-continued

|  |  |  |  |  |  |
|---|---|---|---|---|---|
|  |  | monomer | 3G (23), HEMA (22.9) | 3G (19), HEMA (20.9) | 3G (24), HEMA (24.9) | 3G (24), HEMA (24.9) |
|  |  | Other component | BMOV (0.1) | BMOV (0.1) | BMOV (0.1) | BMOV (0.1) |
|  | Second agent | (C) Silane coupling agent | MPTES (8) | MPTES (8) | MPTES (8) | MPTES (8) |
|  |  | (D) Borate compound | PhB—Na (4) | PhB—Na (4) | PhB—Na (4) | PhB—Na (4) |
|  |  | (E) Water | Water (25) | Water (25) | Water (25) | Water (25) |
|  |  | Organic solvent | Acetone (150) IPA (60) | Acetone (150) IPA (60) | Acetone (150) IPA (60) | Acetone (150) IPA (60) |
|  |  | Other component | PEROCTA H (3) | PEROCTA H (3) | PEROCTA H (3) | PEROCTA H (3) |

TABLE 3

|  |  | Example 27 | Example 28 | Example 29 | Example 30 |
|---|---|---|---|---|---|
| First agent | (A) Acidic group-containing polymerizable monomer | MDP (15) | MDP (15) | MDP (15) | MDP (15) |
|  | (B) Sulfur atom-containing polymerizable monomer | MTU-6 (0.1) | MTU-6 (0.1) | MTU-6 (0.1) | MTU-6 (0.01) |
|  | Organic solvent | Acetone (150) | Acetone (150) | Acetone (150) | Acetone (150) |
|  | Other polymerizable monomer | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.99) |
|  | Other component | BMOV (0.1) | BMOV (0.1) | BMOV (0.1) | BMOV (0.1) |
| Second agent | (C) Silane coupling agent | MPTES (8) | MPTES (8) | MPTES (8) | MPTES (8) |
|  | (D) Borate compound | PhB—Na (4) | PhB—Na (4) | PhB—Na (4) | PhB—Na (1) |
|  | (E) Water | Water (10) | Water (45) | Water (150) | Water (25) |
|  | Organic solvent | Acetone (161) IPA (64) | Acetone (136) IPA (54) | Acetone (61) IPA (24) | Acetone (153) IPA (60) |
|  | Other component | PEROCTA H (3) | PEROCTA H (3) | PEROCTA H (3) | PEROCTA H (3) |

|  |  | Example 31 | Example 32 | Example 33 | Example 34 |
|---|---|---|---|---|---|
| First agent | (A) Acidic group-containing polymerizable monomer | MDP (15) | MDP (15) | MDP (15) | MDP (15) |
|  | (B) Sulfur atom-containing polymerizable monomer | MTU-6 (1) | MTU-6 (1) | MMT-11 (1) | MMT-11 (0.1) |
|  | Organic solvent | Acetone (150) | Acetone (150) | Acetone (150) | Acetone (150) |
|  | Other polymerizable monomer | BisGMA (36), 3G (24), HEMA (24) | BisGMA (36), 3G (24), HEMA (24) | BisGMA (36), 3G (24), HEMA (24) | BisGMA (36), 3G (24), HEMA (24.9) |
|  | Other component | BMOV (0.1) | BMOV (0.1) | BMOV (0.1) | BMOV (0.1) |
| Second agent | (C) Silane coupling agent | MPTES (8) | MPTES (8) | MPTES (3) | MPTES (20) |
|  | (D) Borate compound | PhB—Na (8) | PhB-TEOA (25) | PhB—Na (4) | PhB—Na (4) |
|  | (E) Water | Water (25) | Water (25) | Water (25) | Water (25) |
|  | Organic solvent | Acetone (146) IPA (60) | Acetone (129) IPA (60) | Acetone (155) IPA (60) | Acetone (138) IPA (60) |
|  | Other component | PEROCTA H (3) | PEROCTA H (3) | PEROCTA H (3) | PEROCTA H (3) |

TABLE 4

|  |  | Comparative Example 1 | Comparative Example 2 | Comparative Example 3 | Comparative Example 4 |
|---|---|---|---|---|---|
| First agent | (A) Acidic group-containing polymerizable monomer | — | MDP (15) | MDP (15) | MDP (15) |
|  | (B) Sulfur atom-containing polymerizable monomer | MTU-6 (0.1) | — | MTU-6 (0.1) | MTU-6 (0.1) |
|  | (C) Silane coupling agent |  |  | — |  |
|  | (D) Borate compound |  |  | — |  |
|  | (E) Water |  |  | — |  |
|  | Organic solvent | Acetone (150) | Acetone (150) | Acetone (150) | Acetone (150) |
|  | Other polymerizable monomer | BisGMA (42), 3G (28), HEMA (29.9) | BisGMA (36), 3G (24), HEMA (25) | BisGMA (36), 3G (24), HEMA (24.9) | BisGMA (36), 3G (24), HEMA (24.9) |
|  | Other component | BMOV (0.1) | BMOV (0.1) | BMOV (0.1) | BMOV (0.1) |
| Second agent | (B) Sulfur atom-containing polymerizable monomer |  |  |  | — |
|  | (C) Silane coupling agent | MPS (8) | MPS (8) | — | MPS (8) |
|  | (D) Borate compound | PhB-TEOA (4) | PhB-TEOA (4) | PhB-TEOA (4) | — |
|  | (E) Water | Water (25) | Water (25) | Water (25) | Water (25) |
|  | Organic solvent | Acetone (150) IPA (60) | Acetone (150) IPA (60) | Acetone (158) IPA (60) | Acetone (154) IPA (60) |

TABLE 4-continued

| | | Comparative Example 5 | Comparative Example 6 | Comparative Example 7 | Comparative Example 8 |
|---|---|---|---|---|---|
| | Other component | PEROCTA H (3) | PEROCTA H (3) | PEROCTA H (3) | PEROCTA H (3) |
| First agent | (A) Acidic group-containing polymerizable monomer | MDP (15) | MDP (15) | MDP (15) | MDP (15) |
| | (B) Sulfur atom-containing polymerizable monomer | MTU-6 (0.1) | MTU-6 (0.1) | MTU-6 (0.1) | MTU-6 (0.1) |
| | (C) Silane coupling agent | — | — | MPS (8) | — |
| | (D) Borate compound | — | — | — | PhB-TEOA (4) |
| | (E) Water | — | — | — | — |
| | Organic solvent | Acetone (150) | Acetone (146) | Acetone (142) | Acetone (146) |
| | Other polymerizable monomer | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
| | Other component | BMOV (0.1) | CQ (2), DMBE (2) | BMOV (0.1) | BMOV (0.1) |
| Second agent | (B) Sulfur atom-containing polymerizable monomer | — | — | — | — |
| | (C) Silane coupling agent | MPS (8) | MPS (8) | — | MPS (8) |
| | (D) Borate compound | PhB-TEOA (4) | — | PhB-TEOA (4) | — |
| | (E) Water | — | Water (25) | Water (25) | Water (25) |
| | Organic solvent | Acetone (175) IPA (60) | Acetone (150) IPA (60) | Acetone (158) IPA (60) | Acetone (154) IPA (60) |
| | Other component | PEROCTA H (3) | — | PEROCTA H (3) | PEROCTA H (3) |

| | | Comparative Example 9 | Comparative Example 10 | Comparative Example 11 | Comparative Example 12 | Comparative Example 13 |
|---|---|---|---|---|---|---|
| First agent | (A) Acidic group-containing polymerizable monomer | MDP (15) | MDP (15) | MDP (15) | MDP (15) | MDP (15) |
| | (B) Sulfur atom-containing polymerizable monomer | MTU-6 (0.1) | MTU-6 (0.1) | MTU-6 (0.1) | MTU-6 (0.1) | MTU-6 (0.1) |
| | (C) Silane coupling agent | — | — | MPS (8) | — | — |
| | (D) Borate compound | — | — | PhB-TEOA (4) | — | — |
| | (E) Water | Water (25) | — | Water (25) | — | — |
| | Organic solvent | Acetone (125) | Acetone (150) | Acetone (300) | Acetone (147) | Acetone (150) |
| | Other polymerizable monomer | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
| | Other component | BMOV (0.1) | BMOV (0.1) | BMOV (0.1) | BPO (3) | — |
| Second agent | (B) Sulfur atom-containing polymerizable monomer | — | MTU-6 (0.05) | — | — | — |
| | (C) Silane coupling agent | MPS (8) | MPS (8) | — | MPS (8) | MPS (8) |
| | (D) Borate compound | PhB-TEOA (4) | PhB-TEOA (4) | — | — | — |
| | (E) Water | — | Water (25) | — | Water (25) | Water (25) |
| | Organic solvent | Acetone (175) IPA (60) | Acetone (150) IPA (60) | — | Acetone (153) IPA (60) | Acetone (153) IPA (60) |
| | Other component | PEROCTA H (3) | PEROCTA H (3) | — | DEPT (4) | PTSNa (4) |

| | | Comparative Example 14 | Comparative Example 15 | Comparative Example 16 | Comparative Example 17 |
|---|---|---|---|---|---|
| First agent | (A) Acidic group-containing polymerizable monomer | MDP (15) | MDP (15) | MDP (15) | MDP (15) |
| | (B) Sulfur atom-containing polymerizable monomer | MTU-6 (0.1) | MTU-6 (0.1) | MTU-6 (0.1) | MTU-6 (0.1) |
| | (C) Silane coupling agent | — | — | — | — |
| | (D) Borate compound | — | — | — | — |
| | (E) Water | — | — | — | — |
| | Organic solvent | Acetone (70) | Acetone (100) | Acetone (270) | Acetone (60) |
| | Other polymerizable monomer | BisGMA (36), 3G (24), HEMA (24.9) | BisGMA (36), 3G (24), HEMA (24.9) | BisGMA (36), 3G (24), HEMA (24.9) | BisGMA (36), 3G (24), HEMA (24.9) |
| | Other component | Cu—AcAc (0.2) MBI (2) | Cu—AcAc (0.2) MBI (2) | Cu—AcAc (0.2) MBI (2) | BPO (3) |
| Second agent | (B) Sulfur atom-containing polymerizable monomer | — | — | — | — |
| | (C) Silane coupling agent | MPS (8) | MPS (8) | MPS (8) | MPS (8) |
| | (D) Borate compound | — | — | — | — |
| | (E) Water | Water (25) | Water (25) | Water (25) | Water (25) |
| | Organic solvent | Acetone (75) IPA (60) | Acetone (155) IPA (10) | Acetone (185) IPA (150) | Acetone (106) IPA (20) |
| | Other component | PEROCTA H (4) | PEROCTA H (4) | PEROCTA H (4) | DEPT (4) |

TABLE 5

| | Initial adhesive strength (MPa) | | | | | | | | |
|---|---|---|---|---|---|---|---|---|---|
| | Adherend 2 | | | | | | | | |
| | Composite resin | | | | Resin cement | | | | |
| | Adherend 1 | | | | | | | | |
| | Tooth substance (enamel) | Tooth substance (dentin) | Tooth substance (enamel) | Tooth substance (dentin) | Noble metal alloy | Base metal alloy | Silica-based oxide (porcelain) | Composite resin material (ESTELITE BLOCK) | Metal oxide (zirconia ceramics) |
| Example 1 | 17 | 15 | 19 | 16 | 24 | 23 | 25 | 23 | 24 |
| Example 2 | 26 | 25 | 27 | 26 | 30 | 32 | 33 | 28 | 32 |
| Example 3 | 25 | 25 | 26 | 25 | 30 | 32 | 34 | 28 | 32 |
| Example 4 | 24 | 23 | 25 | 24 | 29 | 31 | 33 | 27 | 31 |
| Example 5 | 24 | 23 | 25 | 24 | 29 | 30 | 34 | 28 | 31 |
| Example 6 | 22 | 18 | 21 | 20 | 28 | 30 | 31 | 25 | 28 |
| Example 7 | 25 | 25 | 26 | 25 | 29 | 31 | 33 | 28 | 31 |
| Example 8 | 21 | 18 | 22 | 20 | 28 | 30 | 32 | 25 | 28 |
| Example 9 | 24 | 23 | 24 | 24 | 30 | 32 | 31 | 27 | 30 |
| Example 10 | 25 | 24 | 25 | 24 | 30 | 31 | 32 | 27 | 31 |
| Example 11 | 20 | 17 | 20 | 18 | 28 | 30 | 31 | 26 | 29 |
| Example 12 | 26 | 25 | 27 | 25 | 30 | 31 | 34 | 29 | 32 |
| Example 13 | 27 | 25 | 27 | 26 | 30 | 32 | 33 | 28 | 32 |
| Example 14 | 17 | 15 | 20 | 16 | 28 | 28 | 29 | 26 | 30 |
| Example 15 | 22 | 21 | 24 | 22 | 30 | 31 | 31 | 28 | 32 |
| Example 16 | 24 | 25 | 26 | 25 | 30 | 30 | 32 | 27 | 32 |
| Example 17 | 23 | 21 | 25 | 24 | 29 | 30 | 33 | 27 | 31 |
| Example 18 | 29 | 28 | 29 | 28 | 32 | 33 | 35 | 30 | 34 |
| Example 19 | 26 | 25 | 27 | 27 | 30 | 31 | 32 | 28 | 31 |
| Example 20 | 29 | 28 | 28 | 28 | 31 | 33 | 35 | 29 | 33 |
| Example 21 | 26 | 25 | 27 | 26 | 30 | 32 | 32 | 28 | 31 |
| Example 22 | 28 | 26 | 27 | 26 | 31 | 33 | 34 | 29 | 33 |
| Example 23 | 29 | 29 | 29 | 28 | 31 | 33 | 35 | 29 | 33 |
| Example 24 | 29 | 28 | 29 | 27 | 30 | 32 | 35 | 28 | 31 |
| Example 25 | 19 | 17 | 20 | 19 | 27 | 21 | 32 | 28 | 21 |
| Example 26 | 24 | 23 | 25 | 22 | 30 | 30 | 33 | 28 | 30 |

TABLE 6

| | Initial adhesive strength (MPa) | | | | | | | | |
|---|---|---|---|---|---|---|---|---|---|
| | Adherend 2 | | | | | | | | |
| | Composite resin | | | | Resin cement | | | | |
| | Adherend 1 | | | | | | | | |
| | Tooth substance (enamel) | Tooth substance (dentin) | Tooth substance (enamel) | Tooth substance (dentin) | Noble metal alloy | Base metal alloy | Silica-based oxide (porcelain) | Composite resin material (ESTELITE BLOCK) | Metal oxide (zirconia ceramics) |
| Example 27 | 20 | 24 | 21 | 23 | 30 | 32 | 32 | 28 | 31 |
| Example 28 | 26 | 25 | 27 | 26 | 29 | 28 | 34 | 29 | 29 |
| Example 29 | 23 | 20 | 23 | 21 | 28 | 28 | 32 | 28 | 28 |
| Example 30 | 21 | 20 | 22 | 21 | 26 | 28 | 28 | 27 | 26 |
| Example 31 | 25 | 24 | 25 | 24 | 32 | 31 | 35 | 29 | 31 |
| Example 32 | 22 | 21 | 23 | 20 | 30 | 30 | 31 | 27 | 29 |
| Example 33 | 25 | 24 | 25 | 24 | 31 | 31 | 31 | 28 | 31 |
| Example 34 | 25 | 25 | 26 | 25 | 29 | 32 | 33 | 28 | 31 |
| Comparative Example 1 | 4 | 3 | 3 | 3 | 26 | 12 | 15 | 18 | 12 |
| Comparative Example 2 | 24 | 20 | 25 | 22 | 10 | 31 | 33 | 27 | 30 |
| Comparative Example 3 | 25 | 25 | 25 | 24 | 30 | 32 | 3 | 10 | 32 |
| Comparative Example 4 | 10 | 5 | 4 | 3 | 7 | 9 | 9 | 8 | 7 |
| Comparative Example 5 | 7 | 12 | 8 | 12 | 28 | 30 | 14 | 17 | 30 |
| Comparative Example 6 | 25 | 24 | 4 | 3 | 6 | 7 | 8 | 8 | 8 |
| Comparative Example 7 | 24 | 23 | 24 | 23 | 29 | 28 | 30 | 27 | 30 |
| Comparative Example 8 | 22 | 20 | 23 | 21 | 29 | 29 | 29 | 26 | 30 |
| Comparative Example 9 | 26 | 25 | 25 | 25 | 29 | 30 | 31 | 26 | 29 |
| Comparative Example 10 | 24 | 20 | 24 | 22 | 28 | 31 | 33 | 27 | 30 |
| Comparative Example 11 | 22 | 20 | 23 | 22 | 29 | 29 | 30 | 26 | 30 |
| Comparative Example 12 | 12 | 7 | 13 | 8 | 27 | 27 | 28 | 26 | 27 |
| Comparative Example 13 | 14 | 13 | 22 | 21 | 28 | 29 | 29 | 28 | 29 |
| Comparative Example 14 | 20 | 18 | 22 | 20 | — | — | — | — | — |
| Comparative Example 15 | 20 | 17 | 21 | 19 | — | — | — | — | — |
| Comparative Example 16 | 13 | 10 | 15 | 11 | — | — | — | — | — |
| Comparative Example 17 | 10 | 6 | 12 | 9 | — | — | — | — | — |

TABLE 7

Adhesive strength after long-term storage (MPa)

| | Composite resin Adherend 1 | | | | Resin cement Adherend 1 | | | | | Appearance after long-term storage | |
|---|---|---|---|---|---|---|---|---|---|---|---|
| | Tooth substance (enamel) | Tooth substance (dentin) | Tooth substance (enamel) | Tooth substance (dentin) | Noble metal alloy | Base metal alloy | Silica-based oxide (porcelain) | Composite resin material (ESTELITE BLOCK) | Metal oxide (zirconia ceramics) | First agent | Second agent |
| Example 1 | 13 | 10 | 14 | 11 | 22 | 20 | 10 | 22 | 20 | No change | No change |
| Example 2 | 20 | 18 | 21 | 19 | 28 | 29 | 32 | 27 | 28 | No change | No change |
| Example 3 | 19 | 17 | 20 | 18 | 28 | 29 | 20 | 23 | 28 | No change | No change |
| Example 4 | 17 | 14 | 19 | 15 | 27 | 28 | 10 | 11 | 27 | No change | No change |
| Example 5 | 17 | 13 | 18 | 15 | 27 | 27 | 14 | 18 | 27 | No change | No change |
| Example 6 | 18 | 14 | 19 | 15 | 26 | 27 | 30 | 24 | 24 | No change | No change |
| Example 7 | 17 | 12 | 20 | 15 | 24 | 23 | 26 | 24 | 23 | No change | No change |
| Example 8 | 15 | 14 | 16 | 15 | 26 | 27 | 31 | 24 | 24 | No change | No change |
| Example 9 | 18 | 16 | 18 | 17 | 28 | 29 | 29 | 26 | 26 | No change | No change |
| Example 10 | 19 | 17 | 19 | 17 | 28 | 28 | 31 | 26 | 27 | No change | No change |
| Example 11 | 15 | 12 | 15 | 14 | 26 | 27 | 29 | 25 | 25 | No change | No change |
| Example 12 | 19 | 17 | 21 | 18 | 28 | 29 | 25 | 23 | 28 | No change | No change |
| Example 13 | 20 | 18 | 21 | 19 | 28 | 29 | 28 | 25 | 28 | No change | No change |
| Example 14 | 13 | 10 | 14 | 12 | 26 | 24 | 29 | 25 | 25 | No change | No change |
| Example 15 | 16 | 14 | 17 | 15 | 28 | 28 | 31 | 27 | 27 | No change | No change |
| Example 16 | 19 | 18 | 20 | 19 | 28 | 28 | 32 | 27 | 27 | No change | No change |
| Example 17 | 18 | 15 | 19 | 17 | 27 | 27 | 32 | 26 | 26 | No change | No change |
| Example 18 | 22 | 20 | 22 | 20 | 30 | 30 | 33 | 28 | 30 | No change | No change |
| Example 19 | 19 | 17 | 20 | 19 | 18 | 28 | 30 | 26 | 27 | No change | No change |
| Example 20 | 22 | 20 | 21 | 20 | 19 | 30 | 33 | 27 | 29 | No change | No change |
| Example 21 | 19 | 17 | 20 | 18 | 28 | 29 | 30 | 26 | 27 | No change | No change |
| Example 22 | 21 | 18 | 20 | 18 | 29 | 30 | 32 | 27 | 29 | No change | No change |
| Example 23 | 22 | 21 | 22 | 20 | 29 | 30 | 33 | 27 | 29 | No change | No change |
| Example 24 | 22 | 20 | 22 | 19 | 28 | 29 | 33 | 26 | 27 | No change | No change |
| Example 25 | 13 | 12 | 13 | 12 | 25 | 19 | 30 | 24 | 18 | No change | No change |
| Example 26 | 19 | 17 | 20 | 19 | 28 | 28 | 31 | 27 | 27 | No change | No change |

TABLE 8

Adhesive strength after long-term storage (MPa)

| | Composite resin Adherend 1 | | | | Resin cement Adherend 1 | | | | | Appearance after long-term storage | |
|---|---|---|---|---|---|---|---|---|---|---|---|
| | Tooth substance (enamel) | Tooth substance (dentin) | Tooth substance (enamel) | Tooth substance (dentin) | Noble metal alloy | Base metal alloy | Silica-based oxide (porcelain) | Composite resin material (ESTELITE BLOCK) | Metal oxide (zirconia ceramics) | First agent | Second agent |
| Example 27 | 15 | 17 | 16 | 17 | 28 | 29 | 30 | 26 | 27 | No change | No change |
| Example 28 | 20 | 18 | 21 | 19 | 27 | 20 | 24 | 27 | 19 | No change | No change |
| Example 29 | 20 | 18 | 21 | 19 | 28 | 29 | 13 | 24 | 28 | No change | No change |
| Example 30 | 18 | 15 | 18 | 16 | 24 | 25 | 25 | 24 | 24 | No change | No change |
| Example 31 | 20 | 18 | 21 | 20 | 29 | 29 | 31 | 27 | 28 | No change | No change |
| Example 32 | 17 | 15 | 17 | 15 | 24 | 24 | 10 | 24 | 24 | No change | No change |
| Example 33 | 19 | 17 | 20 | 18 | 28 | 25 | 28 | 24 | 24 | No change | No change |
| Example 34 | 20 | 17 | 21 | 18 | 26 | 29 | 31 | 26 | 28 | No change | No change |
| Comparative Example 1 | 3 | 3 | 3 | 3 | 24 | 13 | 20 | 26 | 12 | No change | No change |
| Comparative Example 2 | 18 | 14 | 19 | 15 | 9 | 29 | 31 | 26 | 28 | No change | No change |
| Comparative Example 3 | 19 | 18 | 19 | 17 | 28 | 29 | 3 | 8 | 28 | No change | No change |
| Comparative Example 4 | 8 | 4 | 4 | 3 | 4 | 4 | 5 | 5 | 5 | No change | No change |
| Comparative Example 5 | 7 | 12 | 8 | 12 | 27 | 29 | 13 | 16 | 28 | No change | No change |
| Comparative Example 6 | 19 | 17 | 4 | 3 | 6 | 6 | 9 | 8 | 7 | No change | No change |
| Comparative Example 7 | 16 | 14 | 16 | 15 | 25 | 24 | 4 | 11 | 23 | No change | No change |
| Comparative Example 8 | — | — | — | — | — | — | — | — | — | Gelation | No change |
| Comparative Example 9 | 4 | 8 | 4 | 9 | 21 | 13 | 28 | 21 | 12 | No change | No change |
| Comparative Example 10 | — | — | — | — | — | — | — | — | — | No change | Gelation |
| Comparative Example 11 | — | — | — | — | — | — | — | — | — | Gelation | — |
| Comparative Example 12 | — | — | — | — | — | — | — | — | — | Gelation | No change |
| Comparative Example 13 | 14 | 13 | 22 | 21 | 28 | 29 | 29 | 28 | 29 | No change | No change |

TABLE 9

| | Adhesive strength after endurance test (MPa) | | | | | | | | |
|---|---|---|---|---|---|---|---|---|---|
| | Adherend 2 | | | | | | | | |
| | Composite resin | | | | Resin cement | | | | |
| | | | | | Adherend 1 | | | | |
| | Tooth substance (enamel) | Tooth substance (dentin) | Tooth substance (enamel) | Tooth substance (dentin) | Noble metal alloy | Base metal alloy | Silica-based oxide (porcelain) | Composite resin material (ESTELITE BLOCK) | Metal oxide (zirconia ceramics) |
| Example 1 | 12 | 10 | 13 | 10 | 24 | 5 | 25 | 3 | 4 |
| Example 2 | 24 | 23 | 25 | 23 | 28 | 30 | 30 | 26 | 30 |
| Example 14 | 17 | 15 | 20 | 16 | 28 | 28 | 28 | 24 | 28 |
| Example 15 | 22 | 21 | 24 | 22 | 28 | 31 | 20 | 26 | 31 |
| Example 16 | 24 | 22 | 25 | 23 | 27 | 18 | 20 | 26 | 15 |
| Example 17 | 22 | 20 | 24 | 22 | 26 | 9 | 27 | 25 | 9 |
| Example 18 | 27 | 26 | 27 | 25 | 30 | 31 | 32 | 28 | 32 |
| Example 19 | 24 | 23 | 25 | 24 | 18 | 18 | 29 | 26 | 19 |
| Example 20 | 27 | 26 | 26 | 25 | 19 | 31 | 32 | 27 | 31 |
| Example 21 | 24 | 23 | 25 | 23 | 28 | 30 | 29 | 26 | 29 |
| Example 22 | 26 | 24 | 25 | 23 | 29 | 31 | 31 | 27 | 31 |
| Example 23 | 27 | 27 | 27 | 25 | 29 | 31 | 32 | 27 | 31 |
| Example 24 | 27 | 26 | 27 | 24 | 28 | 8 | 32 | 26 | 9 |
| Example 25 | 16 | 14 | 18 | 18 | 26 | 6 | 31 | 27 | 7 |
| Comparative Example 1 | 2 | 1 | 2 | 1 | 24 | 1 | 12 | 16 | 1 |

TABLE 10

| | Operation time (seconds) | Floating amount of prosthesis (μm) | Curing time at time of mixing (seconds) | Adhesive layer thickness at time of bonding of composite resin (μm) |
|---|---|---|---|---|
| Example 2 | 140 | 19 | 20 | 9 |
| Example 6 | 200 | 16 | 20 | 7 |
| Example 7 | 90 | 23 | 20 | 11 |
| Example 8 | 210 | 20 | 20 | 7 |
| Example 9 | 110 | 34 | 20 | 8 |
| Comparative Example 14 | 40 | — | 40 | 13 |
| Comparative Example 15 | 60 | 90 | 40 | 16 |
| Comparative Example 16 | 300 | — | 40 | 3 |
| Comparative Example 17 | 50 | 30 | 110 | 6 |

The invention claimed is:

1. A two-package dental adhesive composition including a first agent and a second agent, which are divided from each other,
   the two-package dental adhesive composition comprising at least five components including:
   an acidic group-containing polymerizable monomer;
   a sulfur atom-containing polymerizable monomer;
   a silane coupling agent;
   a tetraarylborate compound; and
   water,
   wherein the first agent contains only the acidic group-containing polymerizable monomer and the sulfur atom-containing polymerizable monomer out of the five components,
   wherein the second agent contains only the silane coupling agent, the tetraarylborate compound, and the water out of the five components,
   wherein at least one of the first agent or the second agent further contains an organic solvent,
   wherein the organic solvent comprises at least a low-boiling-point organic solvent having a boiling point of from 50° C. to 65° C. at normal pressure, and a high-boiling-point organic solvent having a boiling point of from 75° C. to 90° C. at normal pressure,
   wherein a blending ratio of the low-boiling-point organic solvent with respect to 100 parts by mass of polymerization-reactive components including at least the acidic group-containing polymerizable monomer, the sulfur atom-containing polymerizable monomer, and the silane coupling agent is from 200 Parts by mass to 400 parts by mass, and
   wherein a blending ratio of the high-boiling-point organic solvent with respect to 100 parts by mass of the polymerization-reactive components is from 25 parts by mass to 120 parts by mass.

2. A two-package dental adhesive composition according to claim 1, wherein a blending ratio of the acidic group-containing polymerizable monomer with respect to 100 parts by mass of all polymerizable monomers including at least the acidic group-containing polymerizable monomer and the sulfur atom-containing polymerizable monomer is from 5 parts by mass to 30 parts by mass.

3. A two-package dental adhesive composition according to claim 1,
   wherein the acidic group-containing polymerizable monomer to be used comprises an acidic group-containing polymerizable monomer represented by general formula (A1) and an acidic group-containing polymerizable monomer represented by general formula (A2), and
   wherein a blending ratio of the acidic group-containing polymerizable monomer represented by the general formula (A2) to a total amount of the acidic group-containing polymerizable monomer represented by the general formula (A1) and the acidic group-containing polymerizable monomer represented by the general formula (A2) is from 3 mass % to 40 mass %:

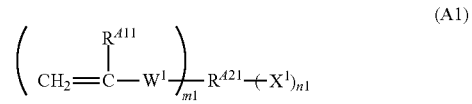

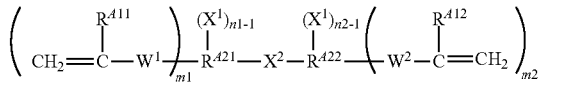
(A2)

in the general formula (A1), $R^{A11}$ represents a hydrogen atom or a methyl group, $W^1$ represents an oxycarbonyl group (—COO—), an iminocarbonyl group (—CONH—), or a phenylene group (—$C_6H_4$—), $R^{A21}$ represents (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, $X^1$ represents a monovalent acidic group, m1 represents an integer of from 1 to 4, n1 represents an integer of from 1 to 6−m1, and m1+n1 represents a valence of $R^{A21}$; and in the general formula (A2), $R^{A11}$ and $R^{A12}$ each independently represent a hydrogen atom or a methyl group, $W^1$ and $W^2$ each independently represent an oxycarbonyl group (—COO—), an iminocarbonyl group (—CONH—), or a phenylene group (—$C_6H_4$—), $R^{A21}$ and $R^{A22}$ each independently represent (i) a bonding site, (ii) a 2- to 6-valent hydrocarbon group having 1 to 30 carbon atoms, or (iii) a 2- to 6-valent organic residue having 1 to 30 carbon atoms and containing at least one bond selected from an ether bond and an ester bond, $X^1$ represents a monovalent acidic group, $X^2$ represents a divalent acidic group, m1 and m2 each independently represent an integer of from 1 to 4, n1 represents an integer of from 1 to 6−m1, n2 represents an integer of from 1 to 6−m2, m1+n1 represents a valence of $R^{A21}$, and m2+n2 represents a valence of $R^{A22}$.

4. A two-package dental adhesive composition according to claim 1, wherein the acidic group-containing polymerizable monomer to be used comprises a long-chain phosphoric acid group-containing polymerizable monomer represented by the general formula (A1) and a short-chain phosphoric acid group-containing polymerizable monomer represented by the general formula (A2):

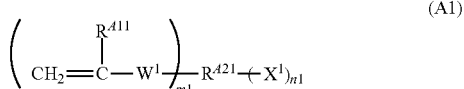
(A1)

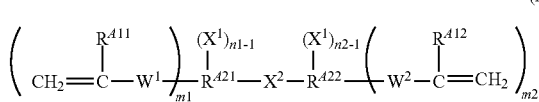
(A2)

in the general formula (A1), $R^{A11}$ represents a hydrogen atom or a methyl group, $W^1$ represents an oxycarbonyl group (—COO—), an iminocarbonyl group (—CONH—), or a phenylene group (—$C_6H_4$—), $R^{A21}$ represents a 2- to 6-valent chain hydrocarbon group having 6 to 14 carbon atoms in a main chain thereof, or a 2- to 6-valent chain organic residue containing at least one bond selected from an ether bond and an ester bond in a main chain thereof and having 6 to 14 atoms in the main chain, $X^1$ represents a dihydrogen phosphate monoester group {—O—P(=O)(OH)$_2$} or a phosphono group {—P(=O)(OH)$_2$}, m1 represents an integer of from 1 to 4, n1 represents an integer of from 1 to 6−m1, and m1+n1 represents a valence of $R^{A21}$; and in the general formula (A2), $R^{A11}$ and $R^{A12}$ each independently represent a hydrogen atom or a methyl group, $W^1$ and $W^2$ each independently represent an oxycarbonyl group (—COO—), an iminocarbonyl group (—CONH—), or a phenylene group (—$C_6H_4$—), $R^{A21}$ and $R^{A22}$ each independently represent a 2- to 6-valent chain hydrocarbon group having 2 to 4 carbon atoms in a main chain thereof, or a 2- to 6-valent chain organic residue containing at least one bond selected from an ether bond and an ester bond in a main chain thereof and having 2 to 4 atoms in the main chain, $X^1$ represents a monovalent acidic group, $X^2$ represents a hydrogen phosphate diester group {(—O—)$_2$P(=O)OH} or a phosphinico group {=P(=O)OH}, m1 and m2 each independently represent an integer of from 1 to 4, m1+n1 represents a valence of $R^{A21}$, m2+n2 represents a valence of $R^{A22}$, n1 represents an integer of from 1 to 6−m1, and n2 represents an integer of from 1 to 6−m2.

5. A two-package dental adhesive composition according to claim 1, wherein the silane coupling agent comprises a compound represented by general formula (C1):

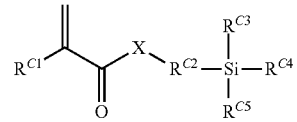
(C1)

in the general formula (C1), X represents an oxygen atom or a nitrogen atom, $R^{C1}$ represents a methyl group or a hydrogen atom, $R^{C2}$ represents an alkylene group having 1 to 10 carbon atoms, and $R^{C3}$, $R^{C4}$, and $R^{C5}$ each independently represent an alkyl group having 1 to 10 carbon atoms or an alkoxyl group having 1 to 10 carbon atoms, provided that at least one group selected from $R^{C3}$, $R^{C4}$, and $R^{C5}$ is an alkoxy group having 2 to 4 carbon atoms.

6. A two-package dental adhesive composition according to claim 5, wherein, in the general formula (C1), $R^{C3}$, $R^{C4}$, and $R^{C5}$ each independently represent an alkoxyl group having 2 to 4 carbon atoms.

7. A two-package dental adhesive composition according to claim 1, wherein the tetraarylborate compound comprises an alkali metal salt of tetraarylborate.

8. A two-package dental adhesive composition according to claim 1, wherein a blending ratio of the tetraarylborate compound with respect to 100 parts by mass of the silane coupling agent is from 1 part by mass to 300 parts by mass.

9. A two-package dental adhesive composition according to claim 1, wherein a blending ratio of the water with respect to 100 parts by mass of the silane coupling agent is from 20 parts by mass to 1,500 parts by mass.

10. A two-package dental adhesive composition according to claim 1, wherein a blending ratio of the water with respect to 100 parts by mass of the polymerization-reactive components is from 5 parts by mass to 50 parts by mass.

11. A two-package dental adhesive composition according to claim 1, wherein a mass ratio of the low-boiling-point organic solvent to the high-boiling-point organic solvent is from 2 to 12.

12. A two-package dental adhesive composition according to claim 1, further comprising an organic peroxide and a vanadium compound.

13. A two-package dental adhesive composition according to claim 1, wherein
in each of (i) a case in which the two-package dental adhesive composition contains only the tetraarylborate compound blended into the second agent as a chemical polymerization initiator, and (ii) a case in which the two-package dental adhesive composition contains each of the tetraarylborate compound blended into the second agent, and a chemical polymerization initiator other than the tetraarylborate compound, which is blended into at least one of the first agent or the second agent, as the chemical polymerization initiator,
when a mixture obtained by mixing, at 23° C., only a whole amount of the polymerization-reactive components and a whole amount of the chemical polymerization initiator is prepared,
a curing time commencing immediately after the mixing and ending on completion of curing of the mixture is 60 seconds or less.

14. A two-package dental adhesive composition according to claim 1,
wherein the first agent further contains the organic solvent, and
wherein a blending ratio of the organic solvent in the first agent is from 30 mass % to 90 mass %.

15. A two-package dental adhesive composition according to claim 1,
wherein the second agent further contains the organic solvent, and
wherein a blending ratio of the organic solvent in the second agent is from 10 mass % to 99 mass %.

16. A two-package dental adhesive composition according to claim 1,
wherein the first agent and the second agent each further contain the organic solvent, and
wherein a ratio of a total amount of the organic solvent to a total amount of the first agent and the second agent is from 63 mass % to 85 mass %.

* * * * *